(12) United States Patent
Termin et al.

(10) Patent No.: US 7,276,526 B2
(45) Date of Patent: Oct. 2, 2007

(54) SUBSTITUTED THIAZOLES AND OXAZOLES AS CORTICOTROPIN RELEASING HORMONE LIGANDS

(75) Inventors: Andreas Termin, Encinitas, CA (US); Peter Grootenhuis, San Diego, CA (US); Dean Wilson, San Diego, CA (US); Valentina Molteni, San Diego, CA (US); Long Mao, San Diego, CA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 769 days.

(21) Appl. No.: 10/192,055

(22) Filed: Jul. 10, 2002

(65) Prior Publication Data
US 2003/0114502 A1  Jun. 19, 2003

Related U.S. Application Data

(60) Provisional application No. 60/305,067, filed on Jul. 13, 2001.

(51) Int. Cl.
*C07D 417/08* (2006.01)
*A61K 31/427* (2006.01)

(52) U.S. Cl. ............... 514/342; 514/365; 514/374; 546/269.7; 548/202; 548/203; 548/235; 548/236

(58) Field of Classification Search ............. 548/202, 548/203, 235, 236; 546/269.7; 514/342, 514/365, 374
See application file for complete search history.

(56) References Cited

U.S. PATENT DOCUMENTS 5,464,847 A  11/1995  Courtemanche et al. .... 514/342

FOREIGN PATENT DOCUMENTS

| WO | WO92/16527 | 10/1992 |
|----|------------|---------|
| WO | WO95/10506 | 4/1995 |
| WO | WO97/35539 | 10/1997 |
| WO | WO97/35846 | 10/1997 |
| WO | WO97/44308 | 11/1997 |
| WO | WO98/03510 | 1/1998 |
| WO | WO99/01439 | 1/1999 |
| WO | WO99/01454 | 1/1999 |
| WO | WO99/11643 | 3/1999 |
| WO | WO99/51608 | 10/1999 |
| WO | WO 00/01675 | 1/2000 |

OTHER PUBLICATIONS

Kasahara et al., English Translation of WO 92/16527 published Oct. 1992.*
Mitchell, PubMed Abstract (Neurosci Biobehav Rev. 22(5):635-51) Sep. 1998.*
J. Rivier et al., Proc. Nat. Acad. Sci. (USA), 80:4851 (1983).
W. Vale et al., Science, 213:1394 (1981).
W. Vale et al., Rec. Prog. Horm. Res., 39:245 (1983).
G.F. Koob, Persp. Behav. Med., 2:39 (1985).
E.B. Desouza et al., J. Neurosci., 5:3189 (1985).
J.E. Blalock, Physiological Reviews, 69:1 (1989).
J.E. Mortey, Life Sci., 41:527 (1987).
E.B. Desouza, Hosp. Practice, 23:59 (1988).
C.B. Nemeroff et al., Science, 226:1342 (1984).
C.M. Banki et al., Am. J. Psychiatry, 144:873 (1987).
R.D. France et al., Biol. Psychiatry, 28:86 (1988).
M. Arato et al., Biol. Psychiatry, 25:355 (1989).
C.B. Nemeroff et al., Arch. Gen. Psychiatry, 141:619 (1984).
F. Holsboer et al. Psychoneuroendocrinology, 9:147 (1984).
P.W. Gold et al., New Eng. J. Med., 314:1129 (1986).
R.M. Sapoisky, Arch. Gen. Psychiatry, 46:1047 (1989).
Grigoriadis et al., Neuropsychopharmacology, 2:53 (1989).
D.R. Britton et al., Life Sci., 31:363 (1982).
C.W. Berridge and A.J. Dunn, Regul. Peptides, 16:83 (1986).
C.W. Berridge and A.J. Dunn, Horm. Behav., 21:393 (1987).
Brain Research Reviews, 15:71 (1990).
K.T. Britton et al., Psychopharmacology, 86:170 (1985).
K.T. Britton et al., Psychopharmacology, 94:306 (1988).
N.R. Swerdlow et al., Psychopharmacology, 88:147 (1986).
G.F. Koob and K.T. Britton, Corticotripin-Releasing Factor: Basic and Clinical Studies of a Neuropeptide, E.B. Desouza and C.B. Nemeroff eds., CRC Press, p. 221 (1990).
C. Maillot et al., Gastroenterology, 119, 1569-1579 (2000).
J.R. McCarthy et al., Cuur. Pharm. Res., 5, 289-315 (1999).
P.J. Gilligan et al., J. Medicinal Chem., 43, 1641-1660 (2000).
G.P. Chrousos, Int. J. Obesity, 224, Supp 2, S50-S55 (2000).
E. Webster et al., Ann. N.Y. Acad. Sci., 840, 21-32 (1998).

(Continued)

*Primary Examiner*—Deepak Rao
(74) *Attorney, Agent, or Firm*—Shah R. Makujina; Woodcock Washburn LLP

(57) ABSTRACT

Provided herein are novel substituted thiazoles and oxazoles of the Formula (I):

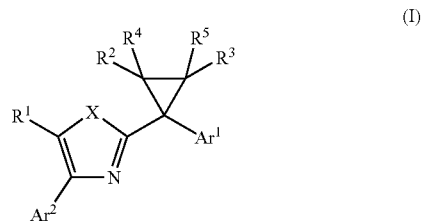

as well as compositions, including pharmaceutical compositions, containing the same, and the use thereof in the treatment of various neurological and psychological disorders, e.g., affective disorder, anxiety and depression, treatable by antagonizing CRF receptors.

8 Claims, No Drawings

OTHER PUBLICATIONS

D.J. Newport and C.B. Nemeroff, Cuur. Opin. Neurobiology, 10, 211-218 (2000).
G. Mastorakos and I. Ilias, Ann. N.Y. Acad. Sci., 900, 95-106 (2000).
M.J. Owens and C.B. Nemeroff, Expert Opin. Invest. Drugs, 8, 1849-1858 (1999).
G.F. Koob, Ann. N.Y. Acad. Sci., 909, 170-185 (2000).
Remington's Pharmaceutical Sciences, 17th ed., Mack Publishing Co, Easton, PA, 1985, p 1418.
Hall et al., J. Org. Chem., 52, 3901-3904 (1987).
J. Med. Chem., 34, 267-276 (1991).
MacGregor et al., J. Org. Chem., 21, 1120-1123 (1956).
M. Fedorynski et al., Org. Prep. Proc. Int., 355-359 (1995).
F. Bailly et al., J. Chem. Soc. Perkin Trans., 1, 2983-2988 (1997).
G. Schwarz, Org. Synth., Coll. vol. 111, 332 (1955).
Wiley et al., Org. Reactions, 6, 367 (1951).
Zeng et al., Combinatorial Chemistry & High Throughput Screening, 1, 101 (1998).
Zeng et al., J. Chromatogr., 794, 1-13 (1998).

* cited by examiner

SUBSTITUTED THIAZOLES AND OXAZOLES AS CORTICOTROPIN RELEASING HORMONE LIGANDS

CROSS-REFERENCE TO RELATED APPLICATIONS

This application claims the benefit of U.S. Provisional Application No. 60/305,067, filed Jul. 13, 2001, the disclosure of which is incorporated herein by reference.

FIELD OF THE INVENTION

This invention relates to compounds which are novel substituted thiazoles and oxazoles, and to the use of such compounds as CRF receptor ligands in the treatment of various CRF-related disorders.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebrospinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C.B. Nemeroff eds., CRC Press p221 (1990)].

It has been further postulated that CRF has a role in cardiovascular or heart-related diseases as well as gastrointestinal disorders arising from stress such as hypertension, tachycardia and congestive heart failure, stroke, irritable bowel syndrome, post-operative ileus and colonic hypersensitivity associated with psychopathological disturbance and stress [for reviews see E. D. DeSouza, C. B. Nemeroff, Editors; Corticotropin-Releasing Factor: Basic and Clinical Studies of a Neuropeptide, E. B. De Souza and C. B. Nemeroff eds., CRC Press p221 (1990) and C. Maillot, M. Million, J. Y. Wei, A. Gauthier, Y. Tache, Gastroenterology, 119, 1569-1579 (2000)].

Over-expression or under -expression of CRF has been proposed as an underlying cause for several medical disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, post-operative ileus and colonic hypersensitivity associated with psycho-pathological disturbance and stress [for reviews see J. R. McCarthy, S. C. Heinrichs and D. E. Grigoriadis, Cuur. Pharm. Res., 5, 289-315 (1999); P. J. Gilligan, D. W. Robertson and R. Zaczek, J. Medicinal Chem., 43, 1641-1660 (2000), G. P. Chrousos, Int. J. Obesity, 24, Suppl. 2, S50-S55 (2000); E. Webster, D. J. Torpy, I. J. Elenkov, G. P. Chrousos, Ann. N. Y. Acad. Sci., 840, 21-32 (1998); D. J. Newport and C. B. Nemeroff, Curr. Opin. Neurobiology, 10, 211-218 (2000); G. Mastorakos and I. Ilias, Ann. N. Y. Acad. Sci., 900, 95-106 (2000); M. J. Owens and C. B. Nemeroff, Expert Opin. Invest. Drugs, 8, 1849-1858 (1999); G. F. Koob, Ann. N. Y. Acad. Sci., 909, 170-185 (2000)].

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; and, WO00/01675.

SUMMARY OF THE INVENTION

The present invention provides novel compounds of Formulae (I), (Ia), (Ib) and (Ic) described hereinbelow which can bind to corticotropin releasing factor receptors, thereby modulating the effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in a mammal.

The present invention also includes pharmaceutical compositions containing the compounds of Formulae (I), (Ia), (Ib) and (Ic) and a pharmceutically acceptable carrier.

Also provided are methods of treating a mammal having a disorder, such as affective disorder, anxiety, or depression, characterized by an abnormal level of corticotropin releasing factor, by administering to the mammal a therapeutically effective amount of a compound of Formulas (I), (Ia), (Ib) or (Ic).

DETAILED DESCRIPTION OF THE INVENTION

This invention is a class of novel compounds which are CRF receptor ligands and which can be represented by Formula (I):

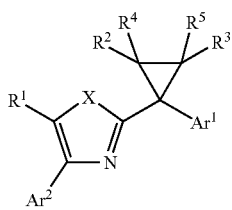
(I)

or a pharmaceutically acceptable salt form thereof, wherein:
X is O or S;
$R^1$ is H, halogen, $C_1$-$C_6$ alkyl, $C_1$-$C_6$ haloalkyl, —CN, —$NO_2$, $C_3$-$C_6$ cycloalkyl, —$NR^6R^7$, —$NR^6COR^7$, —$COR^6$, —$CO_2R^6$, —$OR^6$, —$SR^6$, —$S(O)_nR^6$, —CH(OH)$R^6$, or —$CH_2COR^6$;
each $R^2$ and $R^4$ is, independently, H, halogen, $C_1$-$C_6$ alkyl, $C_1$-$C_6$ haloalkyl, —CN, —$NO_2$, $C_3$-$C_6$ cycloalkyl, —$NR^8R^9$, —$NR^8COR^9$, —$COR^8$, —$C_2R^8$, —$OR^8$, —$SR^8$, —$S(O)_nR^8$, —CH(OH)$R^8$, or —$CH_2COR^8$;
each $R^3$ and $R^5$ is, independently, H, halogen, $C_1$-$C_6$ alkyl, $C_1$-$C_6$ haloalkyl, —CN, —$NO_2$, $C_3$-$C_6$ cycloalkyl, —$NR^{10}R^{11}$, —$NR^{10}COR^{11}$, —$COR^{10}$, —$CO_2R^{10}$, —$OR^{10}$, —$SR^{10}$, —$S(O)_nR^{10}$, —CH(OH)$R^{10}$, or —$CH_2COR^{10}$;
each $R^6$ and $R^7$ is, independently, at each occurance, H, $C_1$-$C_6$ alkyl, $C_1$-$C_6$ haloalkyl, or $C_3$-$C_6$ cycloalkyl, wherein each of said $R^6$ and $R^7$ is optionally substituted with one or more halogen, hydroxyl, or —CN;
each $R^8$ and $R^9$ is, independently, at each occurrence, H, $C_1$-$C_6$ alkyl, $C_1$-$C_6$ haloalkyl, or $C_3$-$C_6$ cycloalkyl, wherein each $R^8$ and $R^9$ is optionally substituted with one or more halogen, hydroxyl, or —CN;
each $R^{10}$ and $R^{11}$ is, independently, at each occurrence, H, $C_1$-$C_6$ alkyl, $C_1$-$C_6$ haloalkyl, or $C_3$-$C_6$ cycloalkyl, wherein each $R^{10}$ and $R^{11}$ is optionally substituted with one or more halogen, hydroxyl, or —CN;
each $R^{12}$ and $R^{13}$ is, independently, at each occurrence, H, —$NH_2$, $C_1$-$C_6$ alkyl, $C_1$-$C_6$ haloalkyl, $C_3$-$C_6$ cycloalkyl, aryl, heteroaryl, or heterocyclyl, wherein each $R^{12}$ and $R^{13}$ is optionally substituted with one or more halogen, hydroxyl, or —CN;
each $R^{14}$ and $R^{15}$ is, independently, at each occurrence, H, —$NH_2$, $C_1$-$C_6$ alkyl, $C_1$-$C_6$ haloalkyl, $C_3$-$C_6$ cycloalkyl, aryl, heteroaryl, or heterocyclyl, wherein each $R^{14}$ and $R^{15}$ is optionally substituted with one or more halogen, hydroxyl, or —CN;
$R^{16}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, aryl-$C_1$-$C_6$ alkyl, —CN, —$CH_2CN$, —$CH_2OR^{12}$, $CH_2NR^{12}R^{13}$, —$CH_2OH$, —$NO_2$, $C_3$-$C_6$ cycloalkyl, —$NR^{12}R^{13}$, —$NR^{12}COR^{13}$, —$NHSO_2R$, —$COR^{12}$, —$CO_2R^{12}$, —$OR^{12}$, —$OC_2H_4OR^{12}$, —$SR^{12}$, —$S(O)_nR^{12}$, —$S(O)_nNR^{12}R^{13}$, —CH(OH)$R^{12}$, —$CH_2COR^{12}$, —OC(O)$R^{12}$, —$OCHR^{12}CO_2R^{13}$, —$OCHR^{12}COR^{13}$, —$NR^{12}CONR^{12}R^{13}$, —$NR^{12}CO_2R^{13}$, —$CONR^{12}R^{13}$, or —CH(OH)C($R^{12}$)$_3$;
$R^{17}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{14}$, $CH_2NR^{14}R^{15}$, —$CH_2OH$, —$NO_2$, $C_3$-$C_6$ cycloalkyl, —$NR^{14}R^{15}$, —$NR^{14}COR^{15}$, —$NHSO_2R$, —$COR^{14}$, —$CO_2R^{14}$, —$OR^{14}$, —$OC_2H_4OR^{14}$, —$SR^{14}$, —$S(O)_nR^{14}$, —$S(O)_nNR^{14}R^{15}$, —CH(OH)$R^{14}$, —$CH_2COR^{14}$, —OC(O)$R^{14}$, —$OCHR^{14}CO_2R^{15}$, —$OCHR^{14}COR^{15}$, —$NR^{14}CONR^{14}R^{15}$, —$NR^{14}CO_2R^{15}$, —$CONR^{14}R^{15}$, or —CH(OH)C($R^{14}$)$_3$;
each $R^{18}$ and $R^{19}$ is, independently, at each occurance, H, $C_1$-$C_6$ alkyl, $C_1$-$C_6$ haloalkyl, or $C_3$-$C_6$ cycloalkyl, wherein each $R^{18}$ and $R^{19}$ is optionally substituted with one or more halogen, hydroxyl, or —CN;
$R^{20}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{21}$, $CH_2NR^{21}R^{22}$, —$CH_2OH$, —$NO_2$, $C_3$-$C_6$ cycloalkyl, —$NR^{21}R^{22}$, —$NR^{21}COR^{22}$, —$NHSO_2R$, —$COR^{21}$, —$CO_2R^{21}$, —$OR^{21}$, —$OC_2H_4OR^{21}$, —$SR^{21}$, —$S(O)_n$ $R^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each $R^{21}$ and $R^{22}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each R$^{21}$ and R$^{22}$ is optionally substituted with one or more halogen, hydroxyl, or —CN;

$R^{23}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{24}$, CH$_2$NR$^{24}$R$^{25}$, —CH$_2$OH, —NO$_2$, C$_3$-C$_6$ cycloalkyl, —NR$^{24}$R$^{25}$, —NR$^{24}$COR$^{25}$, —NHSO$_2$R, —COR$^{24}$, —CO$_2$R$^{24}$, —OR$^{24}$, —OC$_2$H$_4$R$^{24}$, —SR$^{24}$, —S(O)$_n$R$^{24}$, —S(O)$_n$NR$^{24}$R$^{25}$, —CH(OH)R$^{24}$, —CH$_2$COR$^{24}$, —OC(O)R$^{24}$, —OCHR$^{24}$CO$_2$R$^{25}$, —OCHR$^{24}$COR$^{25}$, —NR$^{24}$CONR$^{24}$R$^{25}$, —NR$^{24}$CO$_2$R$^{25}$, —CONR$^{24}$R$^{25}$, or —CH(OH)C(R$^{24}$)$_3$;

each $R^{24}$ and $R^{25}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl or heterocyclyl, wherein each R$^{24}$ and R$^{25}$ is optionally substituted with one or more halogen, hydroxyl, or —CN;

Ar$^1$ is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl 3,4-dihydro-2H-benzo[1,4]oxazine, benzo[1,3]dioxole, or heterocyclyl, wherein Ar$^1$ is optionally substituted with 1 to 5 R$^{16}$ groups; and wherein two of said R$^{16}$ groups, each attached to adjacent carbon atoms of said Ar$^1$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{20}$ groups;

Ar$^2$ is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl, 3,4-dihydro-2H-benzo[1,4]oxazine, benzo[1,3]dioxole, or heterocyclyl, wherein each Ar$^2$ is optionally substituted with 1 to 5 R$^{17}$ groups; and wherein two of said R$^{17}$ groups, each attached to adjacent carbon atoms of said Ar$^2$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{23}$ groups;

n is 0, 1, or 2;

aryl is phenyl or naphthyl, wherein said aryl is optionally substituted with 1 to 10 substituents independently selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, wherein said heteroaryl is optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$ or —S(O)$_n$R$^{18}$, —CH(OH) R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$; and heterocyclyl is saturated or partially saturated heteroaryl, optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —C$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$.

In some embodiments, compounds of the invention are compounds of Formula (I) and pharmaceutically acceptable salts and pro-drugs thereof, wherein:

X is S;

$R^1$ is H, halogen, C$_1$-C$_6$ alkyl, C$_1$-C$_6$ haloalkyl, —CN, —NO$_2$, C$_3$-C$_6$ cycloalkyl, —NR$^6$R$^7$, —NR$^6$COR$^7$, —COR$^6$, —C$_2$R$^6$, —OR$^6$, —SR$^6$, —S(O)$_n$R$^6$, —CH (OH)R$^6$, or —CH$_2$COR$^6$;

Ar$^1$ is phenyl, benzyl, pyridyl, or thienyl, wherein said Ar$^1$ is optionally substituted with 1 to 5 R$^{16}$ groups;

Ar$^2$ is phenyl, benzyl, or pyridyl, wherein said Ar$^2$ is optionally substituted with 1 to 5 R$^{17}$ groups;

$R^{16}$ is, at each occurrence H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, aryl-C$_1$-C$_6$ alkyl, —CN, —COR$^{12}$, —CO$_2$R$^{12}$, —OR$^{12}$, —OC$_2$H$_4$OR$^{12}$, —SR$^{12}$—CH(OH) R$^{12}$, —CH$_2$COR$^{12}$, or —CONR$^{12}$R$^{13}$; and $R^{17}$ is, at each occurrence, H, halogen, C$_1$-C$_6$ alkyl, C$_1$-C$_6$ haloalkyl, —CN, —CH$_2$OH, —NR$^{14}$R$^{15}$, —CO$_2$R$^{14}$, —OR$^{14}$, or —SR$^{14}$.

In other embodiments, compounds of the invention are compounds of Formula (I) and pharmaceutically acceptable salts and pro-drug forms thereof, wherein:

$R^1$ is C$_1$-C$_6$ alkyl;

Ar$^1$ is phenyl optionally substituted with 1 to 5 R$^{16}$ groups; and

Ar$^2$ is phenyl optionally substituted with 1 to 5 R$^{17}$ groups.

In yet other embodiments, compounds of the invention are compounds of Formula (I) and pharmaceutically acceptable salts and pro-drug forms thereof wherein R$^1$ is methyl.

In still other embodiments, compounds of the invention include compounds of Formula (Ia):

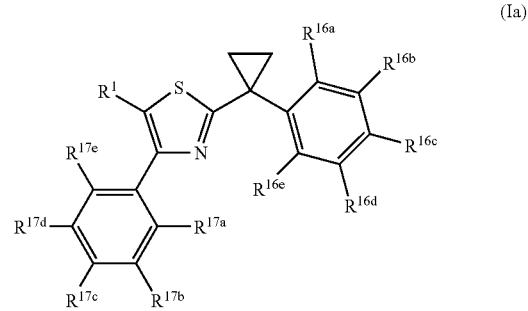

(Ia)

pharmaceutically acceptable salts and pro-drug forms thereof wherein:

$R^1$ is Me, $R^{16a}$ is benzyl, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is m-CN-benzyl, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is —C.CH, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is —C.CH, $R^{16b}$ is H, $R^{16c}$ is H, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is —C.CH, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is F and $R^{17e}$ is H; or $R^1$ is Me, $R^{16a}$ is —C.CH, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is H, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is F, $R^{17b}$ is H, $R^{17c}$ is $CF_3$, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is Br and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Cl, $R^{16b}$ is Cl, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is Cl, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is H, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is F, $R^{17b}$ is H, $R^{17c}$ is F, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is Me, $R^{17d}$ is Cl and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is Me, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is $NMe_2$, $R^{17d}$ is Br and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is $OCHF_2$, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is OEt, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is SMe, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is OMe, $R^{17b}$ is H, $R^{17c}$ is OMe, $R^{17d}$ is Br and $R^{17e}$ is H; or $R^1$ is Me, $R^{16a}$ is Cl, $R^{16b}$ is H, $R^{16c}$ is Cl, $R^{16d}$ H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is F, $R^{17b}$ is H, $R^{17c}$ is $CF_3$, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is F, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is Cl, $R^{17b}$ is H, $R^{17c}$ is H, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is F, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is H, $R^{17b}$ is H, $R^{17c}$ is $CF_3$, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or R$^1$ is Me, R$^{16a}$ is Cl, R$^{16b}$ H, R$^{16c}$ is H, R$^{16d}$ is H, R$^{16e}$ is H, R$^{17a}$ is H, R$^{17b}$ is H, R$^{17c}$ is Me, R$^{17d}$ is H and R$^{17e}$ is H; or R$^1$ is Me, R$^{16a}$ is Cl, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is Cl, R$^{16b}$ is H, R$^{16c}$ is H, R$^{16d}$ is H, R$^{16e}$ is Cl, R$^{17a}$ is H, R$^{17b}$ is H, R$^{17c}$ is OMe, R$^{17d}$ is H and R$^{17e}$ is H; or R$^1$ is Me, R$^{16a}$ is Cl, R$^{16b}$ is H, R$^{16c}$ is H, R$^{16d}$ is H, R$^{16e}$ is F, R$^{17a}$ is OMe, R$^{17b}$ is H, R$^{17c}$ is OMe, R$^{17d}$ is H and R$^{17e}$ is H; or R$^1$ is Me, R$^{16a}$ is CN, R$^{16b}$ is H, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is CN, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is CN, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is CN, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is 5-tetrazolyl, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is CO$_2$Me, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is F, R$^{16b}$ is F, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is F, B$^{16b}$ is F, R$^{16c}$ is H, R$^{16d}$ is H, R$^{17e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is F, R$^{16b}$ is H, R$^{16c}$ is H, R$^{16d}$ is F, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is F, R$^{16b}$ is H, R$^{16c}$ is H, R$^{16d}$ is F, R$^{16e}$ is H, R$^{17a}$ is H, R$^{17b}$ is H, R$^{17c}$ is OCe, R$^{17d}$ is H and R$^{17e}$ is H; or R$^1$ is Me, R$^{16a}$ is F, R$^{16b}$ is H, R$^{16c}$ is H, R$^{16d}$ is F, R$^{16e}$ is H, R$^{17a}$ is H, R$^{17b}$ is H, R$^{17c}$ is Cl, R$^{17d}$ is H and R$^{17e}$ is H; or R$^1$ is Me, R$^{16a}$ is F, R$^{16b}$ is H, R$^{16c}$ is H, R$^{16d}$ is F, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is F, R$^{16b}$ is H, R$^{16c}$ is H, R$^{16d}$ is H, B$^{16e}$ Cl, R$^{17a}$ is H, R$^{17b}$ is H, R$^{17c}$ is Cl, R$^{17d}$ is H and R$^{17e}$ is H; or R$^1$ is Me, R$^{16a}$ is F, R$^{16b}$ is H, R$^{16c}$ is H, R$^{16d}$ is H, R$^{16e}$ is Cl, R$^{17a}$ is H, R$^{17b}$ is H, R$^{17c}$ is OMe, R$^{17d}$ is H and R$^{17e}$ is H; or R$^1$ is Me, R$^{16a}$ is F, R$^{16b}$ is H, R$^{16c}$ is H, R$^{16d}$ is H, R$^{16e}$ is F, R$^{17a}$ is Cl, R$^{17b}$ is H, R$^{17c}$ is Cl, R$^{17d}$ is H and R$^{17e}$ is H; or R$^1$ is Me, R$^{16a}$ is F, R$^{16b}$ is H, R$^{16c}$ is H, R$^{16d}$ is H, R$^{16e}$ is F, R$^{17a}$ is H, R$^{17b}$ is H, R$^{17c}$ is OMe, R$^{17d}$ is H and R$^{17e}$ is H; or R$^1$ is Me, R$^{16a}$ is F, R$^{16b}$ is H, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is F, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ Cl, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is Cl, R$^{16c}$ is H, R$^{16d}$ is H, R$^{16e}$ is H, R$^{17a}$ is H, R$^{17b}$ is H, R$^{17c}$ is Cl, R$^{17d}$ is H and R$^{17e}$ is H; or R$^1$ is Me, R$^{16a}$ is H, R$^{16b}$ is Cl, R$^{16c}$ is H, R$^{16d}$ is H, R$^{16e}$ is H, R$^{17a}$ is H, R$^{17b}$ is H, R$^{17c}$ is Me, R$^{17d}$ is H and R$^{17e}$ is H; or R$^1$ is Me, R$^{16a}$ is H, R$^{16b}$ is F, R$^{16c}$ is H, R$^{16d}$ is F, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ is F, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is Cl, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is Cl, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is H, R$^{16b}$ is H, R$^{16c}$ is Cl, R$^{16d}$ is H, R$^{16e}$ is H, R$^{17a}$ is H, R$^{17b}$ is H, R$^{17c}$ is OEt, R$^{17d}$ is H and R$^{17e}$ is H; or R$^1$ is Me, R$^{16a}$ is H, R$^{16b}$ is H, R$^{16c}$ is F, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is F, R$^{16d}$ is H, R$^{16e}$ is H, R$^{17a}$ is Cl, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is F, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is H, R$^{16b}$ is H, R$^{16c}$ is F, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is F, R$^{17b}$ is H, R$^{17c}$ is H, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is H, R$^{17b}$ is H, R$^{17c}$ is Et, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is Me, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is OMe, R$^{16d}$ is H, R$^{16e}$ is H, R$^{17a}$ Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is OMe, R$^{16d}$ is H, R$^{16e}$ is H, R$^{17a}$ is H, R$^{17b}$ is H, R$^{17c}$ is Me, R$^{17d}$ is H and R$^{17e}$ is H; or R$^1$ is Me, R$^{16a}$ is H, R$^{16b}$ is H, R$^{16c}$ is OMe, R$^{16d}$ is H, R$^{16e}$ is H, R$^{17a}$ is H, R$^{17b}$ is H, R$^{17c}$ is SMe, R$^{17d}$ is H and R$^{17e}$ is H; or $R^1$ is Me, $R^{16a}$ is H, $R^{16b}$ is Me, $R^{16c}$ is F, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is H, $R^{16b}$ is OMe, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is H, $R^{16b}$ is OMe, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is H, $R^{16b}$ is OMe, $R^{16c}$ is OMe, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is I, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is I, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is I, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Me, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Me, $R^{16b}$ is H, $R^{16c}$ is H, $R^{16d}$ is F, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is Me, $R^{16b}$ is H, $R^{16c}$ is H, $R^{16d}$ is H, $R^{16e}$ is F, $R^{17a}$ is Me, $R^{17b}$ is H, $R^{17c}$ is Me, $R^{17d}$ is H and $R^{17e}$ is H; or $R^1$ is Me, $R^{16a}$ is Me, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OBn, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OBn, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $OC_2H_4OMe$, $R_{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $OCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is $OCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is $OCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is $OCF_3$, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is $OCF_3$, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $OCF_3$, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is Me, $R^{16a}$ is $OCH_2C.CH$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $OCH_2CHCH_2$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $OCH_2CN$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is $OCH_2CN$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $OCH_2CO_2Me$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OCH(Me)COMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $OCH(Me)CO_2Et$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $OCH(Me)CO_2Me$, $R^{16b}$ is H, $R^{16c}$ is H, $R^{16d}$ is H, $R^{16e}$ is H, $R^{17a}$ OMe, $R^{17b}$ is H, $R^{17c}$ is OMe, $R^{17d}$ is H and $R^{17e}$ is H; or $R^1$ is Me, $R^{16a}$ is OEt, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OEt, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OEt, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OEt, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OEt, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OH, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is Cl, $R^{17b}$ is H, $R^{17c}$ is OMe, $R^{17d}$ is Me, and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is $CH_2COMe$, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is CH(OH)Me, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is $CH(OH)CMe_3$, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is CN, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is CN, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is COMe, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is CONME$_2$, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is F, $R^{16e}$ is F, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is F, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is CF$_3$, $R^{17b}$ is H, $R^{17c}$ is CF$_3$, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is CH$_2$OH, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is H, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is CN, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is CO$_2$Me, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is F, $R^{17b}$ is H, $R^{17c}$ is CF$_3$, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is CF$_3$, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is Me, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is F and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is I, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Me, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Ph, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Ph, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is SCF$_3$, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is SCF$_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is SCF$_3$, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is SCF$_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is SMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Br, $R^{16a}$ is CF$_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CH$_2$OH, $R^{16a}$ is CF$_3$, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is CHO, $R^{16a}$ is CF$_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is (CH(OH)Me, $R^{16a}$ is CF$_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CN, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is COMe, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is I, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $SCF_3$, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $CH_2OH$, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CHO, $R^{16a}$ is H, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is (C=O)cPr, $R^{16a}$ is H, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CHO, $R^{16a}$ is $OCF_3$, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is CH(OH)Me, $R^{16a}$ is $OCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is CH(OH)Me, $R^{16a}$ is OEt, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is I, $R^{16a}$ is OEt, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Br, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Br, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is $CF_3$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $CH_2CHO$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $CHF_2$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is $CF_3$, $R^{17b}$ is H, $R^{17c}$ is $CF_3$, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is COMe, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is COMe, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is $CO_2Me$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is $CF_3$, $R^{17b}$ is H, $R^{17c}$ is $CF_3$, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $NH_2$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $NO_2$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is SMe, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is SMe, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is Me; or $R^1$ is Me, $R^{16a}$ is Cl, $R^{16b}$ is H, $R^{16c}$ is F, $R^{16d}$ is H, $R^{16e}$ is H, $R^{17a}$ is Me, $R^{17b}$ is H, $R^{17c}$ is Me, $R^{17d}$ is H and $R^{17e}$ is Me; or $R^1$ is Me, $R^{16a}$ is F, $R^{16b}$ is H, $R^{16c}$ is H, $R^{16d}$ is H, $R^{16e}$ is Cl, $R^{17a}$ is Me, $R^{17b}$ is H, $R^{17c}$ is Me, $R^{17d}$ is H and $R^{17e}$ is Me; or $R^1$ is Me, $R^{16a}$ is H, $R^{16b}$ is H, $R^{16c}$ is H, $R^{16d}$ is H, $R^{16e}$ is H, $R^{17a}$ is F, $R^{17b}$ is H, $R^{17c}$ is H, $R^{17d}$ is H and $R^{17e}$ is $CF_3$; or $R^1$ is Me, $R^{16a}$ is OMe, $R^{16b}$ is H, $R^{16c}$ is H, $R^{16d}$ is H, $R^{16e}$ is H, $R^{17a}$ is F, $R^{17b}$ is H, $R^{17c}$ is H, $R^{17d}$ is H and $R^{17e}$ is $CF_3$; or $R^1$ is Me, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is Me.

In other embodiments, compounds of the invention include compounds of Formula (I) and pharmaceutically acceptable salts and pro-drug forms thereof, wherein:

X is O;

$R^1$ is H, halogen, $C_1$-$C_6$ alkyl, $C_1$-$C_6$ haloalkyl, —CN, —$NO_2$, $C_3$-$C_6$ cycloalkyl, —$NR^6R^7$, —$NR^6COR^7$, —$COR^6$, —$CO_2R^6$, —$OR^6$, —$SR^6$ or —$S(O)_nR^6$, —CH(OH)$R^6$, or —$CH_2COR^6$;

$Ar^1$ is phenyl, benzyl, pyridyl, or thienyl, wherein said $Ar^1$ is optionally substituted with 1 to 5 $R^{16}$ groups;

$Ar^2$ is phenyl, benzyl, or pyridyl, wherein $Ar^2$ is optionally substituted with 1 to 5 $R^{17}$ groups;

$R^{16}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, —CN, —$COR^{12}$, —$CO_2R^{12}$, —$OR^{12}$, —$OC_2H_4OR^{12}$, —$SR^{12}$—CH(OH)$R^{12}$, —$CH_2COR^{12}$, or —$CONR^{12}R^{13}$; and $R^{17}$ is, at each occurrence, H, halogen, $C_1$-$C_6$ alkyl, $C_1$-$C_6$ haloalkyl, —CN, —$CH_2OH$, —$NR^{14}R^{15}$, —$CO_2R^{14}$, —$OR^{14}$, or —$SR^{14}$.

In yet other embodiments, compounds of the invention include compounds of Formula (I) and pharmaceutically acceptable salts and pro-drug forms thereof, wherein:

$R^1$ is $C_1$-$C_6$ alkyl;

$Ar^1$ is phenyl optionally substituted with 1 to 5 $R^{16}$ groups; and $Ar^2$ is phenyl optionally substituted with 1 to 5 $R^{17}$ groups.

In still other embodiments, the present invention includes compounds of Formula (Ib):

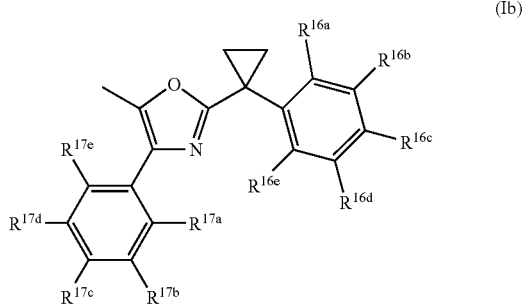

(Ib)

and pharmaceutically acceptable salts and pro-drug forms thereof wherein:

$R^{16a}$ is Cl, $R^{16b}$ is H $R^{16c}$ is Cl $R^{16d}$ is H $R^{16e}$ is H, $R^{17a}$ is H, $R^{17b}$ is $CF_3$, $R^{17c}$ is F, $R^{17d}$ is H and $R^{17e}$ is H; or $R^{16a}$ is Cl, $R^{16b}$ is H $R^{16c}$ is Cl $R^{16d}$ is H $R^{16e}$ is H, $R^{17a}$ is Cl, $R^{17b}$ is H, $R^{17c}$ is Cl, $R^{17d}$ is H and $R^{17e}$ is H; or $R^{16a}$ is Cl, $R^{16b}$ is H $R^{16c}$ is Cl $R^{16d}$ is H $R^{16e}$ is H, $R^{17a}$ is $CF_3$, $R^{17b}$ is H, $R^{17c}$ is H, $R^{17d}$ is H and $R^{17e}$ is F; or $R^{16a}$ is OMe, $R^{16b}$ is H $R^{16c}$ is H $R^{16d}$ is H $R^{16e}$ is H, $R^{17a}$ is Cl, $R^{17b}$ is H, $R^{17c}$ is Cl, $R^{17d}$ is H and $R^{17e}$ is H; or $R^{16a}$ is Cl, $R^{16b}$ is H $R^{16c}$ is Cl $R^{16d}$ is H $R^{16e}$ is H, $R^{17a}$ is Cl, $R^{17b}$ is H, $R^{17c}$ is OMe, $R^{17d}$ is Me and $R^{17e}$ is H.

In further embodiments, compounds of the invention include compounds of Formula (Ic):

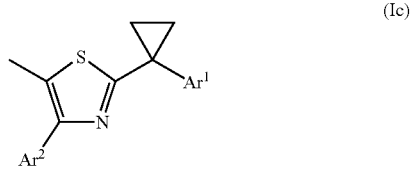

(Ic)

and pharmaceutically acceptable salts and pro-drug forms thereof wherein:

$Ar^1$ is 3-methyl-thien-2-yl and $Ar^2$ is 2,4-dimethoxy-phenyl; or $Ar^1$ is 2-methoxy-phenyl and $Ar^2$ is 2,6-dimethyl-pyrid-3-yl; or $Ar^1$ is 3-methyl-pyrid-2-yl and $Ar^2$ is 3-bromo-4-methoxy-phenyl; or $Ar^1$ is 3-methyl-pyrid-2-yl and $Ar^2$ is 2,4-dichloro-phenyl; or $Ar^1$ is 3-methyl-pyrid-2-yl and $Ar^2$ is 4-trifluoromethyl-phenyl; or $Ar^1$ is 3-chloro-5-trifluoromethyl-pyrid-2-yl and $Ar^2$ is 3-bromo-4-methoxy-phenyl; or $Ar^1$ is 3-chloro-5-trifluoromethyl-pyrid-2-yl and $Ar^2$ is 2,4-dichloro-phenyl; or $Ar^1$ is 3-methyl-pyrid-2-yl and $Ar^2$ is 4-methoxy-phenyl; or $Ar^1$ is 3-methyl-pyrid-2-yl and $Ar^2$ is 4-chloro-phenyl; or $Ar^1$ is 3-methyl-pyrid-2-yl and $Ar^2$ is 2,4-dichloro-phenyl; or $Ar^1$ is 2-methoxy-phenyl and $Ar^2$ is 6-methyl-pyrid-3-yl; or $Ar^1$ is 2-trifluoromethoxy-phenyl and $Ar^2$ is 6-methyl-pyrid-3-yl; or $Ar^1$ is 2,6-dichloro-phenyl and $Ar^2$ is 6-methoxy-pyrid-3-yl; or $Ar^1$ is 2,6-dichloro-phenyl and $Ar^2$ is 2,6-dimethyl-pyrid-3-yl; or $Ar^1$ is 2-trifluoromethyl-phenyl and $Ar^2$ is 2,6-dimethyl-pyrid-3-yl; or $Ar^1$ is 2-trifluoromethoxy-phenyl and $Ar^2$ is 2,6-dimethyl-pyrid-3-yl; or $Ar^1$ is 3-methoxy-pyrid-2-yl and $Ar^2$ is 2-chloro-4-methoxy-5-methyl-phenyl; or $Ar^1$ is 2-bromo-5-methoxy-phenyl and $Ar^2$ is 2,6-dimethyl-pyrid-3-yl.

The term "alkyl" as used herein is meant to refer to a saturated hydrocarbon group (designated by the formula $C_nH2_{n+1}$) which is straight-chained, branched or cyclized ("cycloalkyl"). Alkyl groups can be unsubstituted or substituted so that one or more of its hydrogens are replaced by another chemical group. Example alkyl groups include methyl (Me), ethyl (Et), n-propyl, isopropyl, n-butyl, isobutyl, t-butyl, cyclopentyl, cyclohexyl, norbornyl, and the like. "Alkenyl" refers to hydrocarbon chains of either a straight-chained or branched configuration having one or more unsaturated carbon-carbon bonds. Example alkenyl groups include ethenyl, propenyl, cyclohexenyl, and the like. "Alkynyl" refers to hydrocarbon chains of either a straight-chained or branched configuration having one or more triple carbon-carbon bonds. Example alkynyl groups include ethynyl, propynyl, and the like. "Haloalkyl" refers to branched and straight-chained alkyl groups having one or more halogen substituents. Example haloalkyl groups include $CF_3$, $C_2F_5$, $CHF_2$, $CH_2F$, $CCl_3$, $CHCl_2$, $CH_2Cl$, and the like. The term "alkoxy" refers to an —O-alkyl group. Example alkoxy groups include, methoxy, ethoxy, t-butoxy, and the like. The term "cycloalkyl" refers to cyclized alkyl groups, including mono-,bi- or poly-cyclic ring systems. Example cycloalkyl groups include cyclopropyl, cyclobutyl, cyclopentyl, cyclohexyl, and so forth. "Halo" or "halogen" includes fluoro, chloro, bromo, and iodo.

"Aryl" groups refer to monocyclic or polycyclic aromatic hydrocarbons, including, for example, phenyl, naphthyl, anthracenyl, phenanthrenyl, and the like. Aryl moieties are well known and described, for example, in *Hawley's Condensed Chemical Dictionary* (13 ed.), R. J. Lewis, ed., J. Wiley & Sons, Inc., New York (1997).

"Heteroaryl" groups are monocyclic and polycyclic aromatic hydrocarbons that include at least one sulfur, oxygen, or nitrogen atom ring member. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, and the like.

Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Heterocyclyl" groups are saturated or partially saturated heteroaryl groups. Heterocyclyl groups can be substituted or unsubstituted. Examples of heterocyclyl groups include tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, and the like.

"Substituted" means that one or more hydrogens of a selected atom is replaced with a chemical group other than hydrogen. Substituent selection is typically from the indicated grouping, provided that the selected atom's normal valency is not exceeded, and that the substitution results in a stable compound. By "stable compound" or "stable structure" is meant a compound that is sufficiently robust to survive isolation to a useful degree of purity from a reaction mixture.

In addition to the compounds described and listed hereinabove, this invention provides their corresponding pharmaceutically acceptable salt, radiolabelled, stereoisomeric, and prodrug forms. "Pharmaceutically acceptable salts" of compounds of this invention are also provided herein. The phrase "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically acceptable salt forms of compounds provided herein can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

Radiolabelled compounds, i.e. wherein one or more of the atoms described are replaced by a radioactive isotope of that atom (e.g., C replaced by $^{14}C$ or by $^{11}C$, or H replaced by $^3H$ or $^{18}F$), are also provided for herein. Such compounds have a variety of potential uses, e.g. as standards and reagents in determining the ability of a potential pharmaceutical to bind to neurotransmitter proteins, or for imaging compounds of this invention bound to biological receptors in vivo or in vitro.

Many compounds of the present invention have one or more assymetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms, for example, by chiral chromatography or chemical resolution. It is well known in the art how to prepare optically active forms, such as by resolution of racemic forms or by synthesis from optically active starting materials. All chiral, (enantiomeric and diastereomeric) and racemic forms and all geometric isomeric forms or a structure are intended, unless the specific stereochemistry or isomer form is specifically indicated.

"Prodrugs" are considered to be any covalently bonded carriers which release the active parent drug of Formulae (I), (Ia), (Ib) and (Ic) in vivo when such prodrug is administered to a mammalian subject. Prodrugs of the compounds of Formulae (I), (Ia), (Ib) and (Ic) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of Formulae (I), (Ia), (Ib) and (Ic), and the like.

The term "therapeutically effective amount" of a compound of this invention refers to an amount effective to reduce or eliminate the undesirable symptoms associated with abnormal levels of CRF in a host.

Also provided herein is a pharmaceutical composition comprising one or more of the above compounds and a pharmaceutically acceptable carrier. "Pharmaceutically acceptable carriers" are media generally accepted in the art for the delivery of biologically active agents to animals, in particular, mammals. Such media are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted.

Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences*, 17th ed., Mack Publishing Company, Easton, Pa., 1985, the contents of which are incorporated herein by reference.

Further provided is a method of treating a mammal having a disorder characterized by an abnormal level of CRF where the method involves administrating to a mammal a therapeutically effective amount of one or more compounds of Formulas (I), (Ia), (Ib), and (Ic). Abnormal levels of CRF include, for example, elevated levels of CRF.

Some disorders characterized by abnormal levels of CRF include, for example, affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal. Thus, compounds provided herein which, because of their antagonism of CRF receptors, can alleviate the effects of CRF overexpression are expected to be useful in treating these and other disorders.

This invention thus further provides methods of treating a subject afflicted with a disorder characterized by abnormal levels of CRF (such as overexpression of CRF), such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

According to yet another aspect of the invention, the compounds of Formulae (I), (Ia), (Ib) and (Ic) provided by this invention (including labelled compounds of this invention) are also useful as standards and reagents in determining the ability of a potential pharmaceutical to bind to the CRF receptor.

This invention is described in the following examples, which those of ordinary skill in the art will readily understand fare not limiting on the invention as defined in the claims which follow thereafter.

The compounds provided herein can be, for example and without limitation, made by the synthetic routes and schemes set forth hereinbelow.

Syntheses

The compounds described in the invention may be prepared by one of the general schemes outlined below in Schemes 1-7.

Alpha-bromoketones were synthesized via methods A, B and C (Scheme 1).

(A) Friedel Crafts acylations of the corresponding arenes, with acid chlorides and acid anhydrides with Lewis acid catalysts such as $AlCl_3$, $FeCl_3$ in a solvent such as dichloromethane, chloroform, carbondisulfide. (see: Organikum, Berlin 1991, 18. edition, pages 323-326). The ketones could be halogenated by the action of a halogenating reagent such as $Cl_2$, $Br_2$, $I_2$.

(B) Reaction of aromatic nitriles with Grignard reagents followed by hydrolysis afforded the ketones, which could be halogenated by the action of a halogenating reagent such as $Cl_2$, $Br_2$, $I_2$ (see Hall, S. S., et al. J. Org. Chem. 1987, 52, 3901-3904).

(C) Metallation of a haloarene and reaction with an alkylnitrile followed by hydrolysis to the ketone. The ketones could be halogenated by the action of a halogenating reagent such as $Cl_2$, $Br_2$, $I_2$ (see Ohkawa, S., et al. J. Med. Chem. 1991, 34, 267-276; MacGregor, I. R., et al. J. Org. Chem. 1956, 21, 1120-1123).

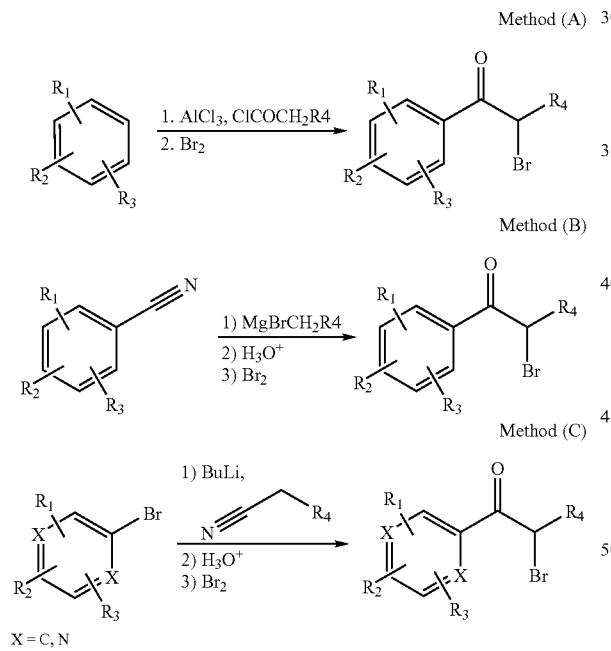

Cyclopropylthioamides were accessed from the correspondent cyclopropylnitriles obtained via methods A and B (Scheme 2).

(A) A phenylacetonitrile was treated with 1-bromo-2-chloro-ethane and base in the presence of a quarternary ammoniun salt as phase transfer catalyst under thermal conditions. (see Fedorynski M. et al. Org. Prep. Proc. Int. 1995, 355-359).

(B) To a solution of an arylhalide (Hal=Br, Cl, F) in THF or toluene was added the cyclopropylnitrile and base such as sodium- or potassiumhexamethyldisilazide (NaHMDS, KHMDS). The reaction mixture was heated to 60-100° C. (see Caron, S. et al. J. Am. Chem. Soc. 2000, 122, 712-713).

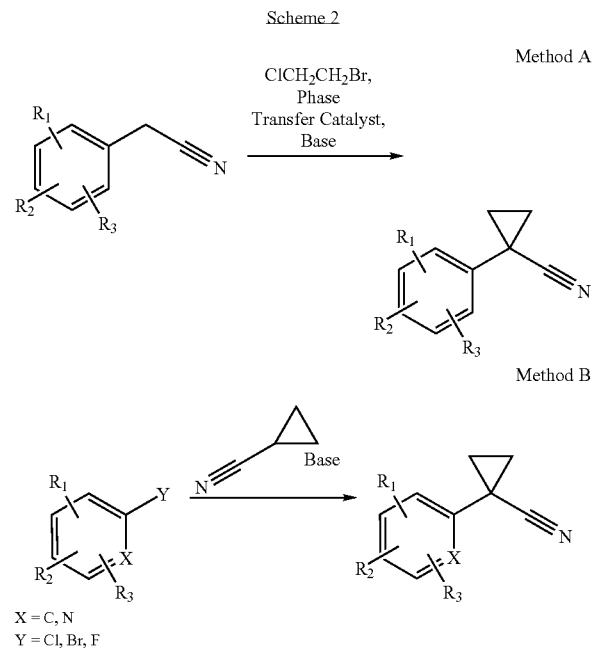

The cyclopropylnitriles were converted to the thioamides by treatment with H2S in solvents such as ethanol and toluene/ethanol mixtures depending on the solubility of the starting material. (see Bailly, F., et al. J. Chem. Soc. Perkin Trans. 1 1997, 2983-2988).

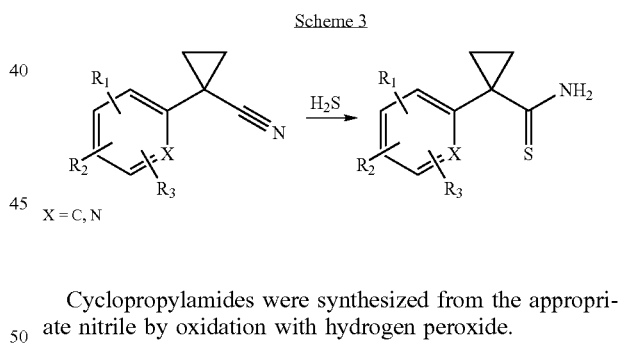

Cyclopropylamides were synthesized from the appropriate nitrile by oxidation with hydrogen peroxide.

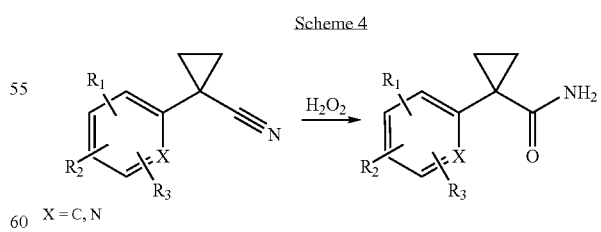

The synthesis of the cyclopropylalkylthiazoles given in the examples followed the classic Hantzsch protocol (see. Schwarz, G., Org. Synth.,Coll.Vol III, 1955, 332 and 'the preparation of Thiazoles, Wiley, R. H., England, D. C. and Behr, L. C., Org. Reactions, 1951, 6, 367) (scheme 5) The cyclopropyloxazoles were synthesized under similar conditions using either DMF as solvent or neat under thermal conditions (scheme 5).

Scheme 5

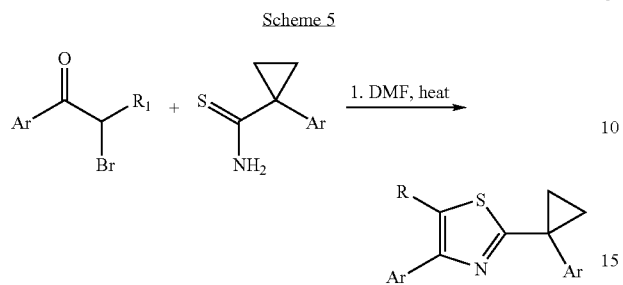

C5 modified alkylthiazoles were synthesized utilizing the bromoacetophenones synthesized by the methods shown in scheme 1 and the appropriate cyclopropyl-thioamides synthesized by methods shown in scheme 2 and 3 to give the 5-unsubstituted alkylthiazoles, followed by lithiation on the 5-position and subsequent reaction with electophiles such as acylhalides, halogens, aldehydes, alkylhalides.

Scheme 6

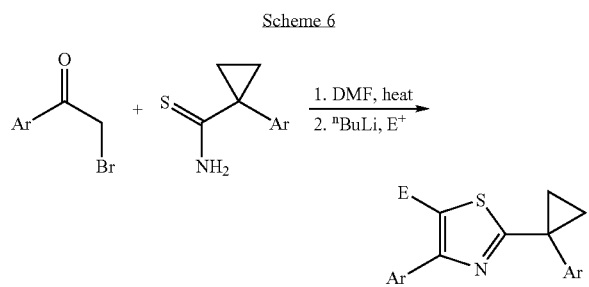

Substituted aryl and heteroaryl rings on both sides of the alkylthiazoles may further be manipulated by zinc, magnesium or palladium coupling reactions as well as lithiation followed by reaction with electrophiles. Alcohols were treated with a base and alkylated, while acids and amines can be reacted with amines and acids respectively with various coupling reagents. Ketones can be converted to the corresponding amines using such reagents as sodium borohydride and related reducing agents (Scheme 7).

Scheme 7

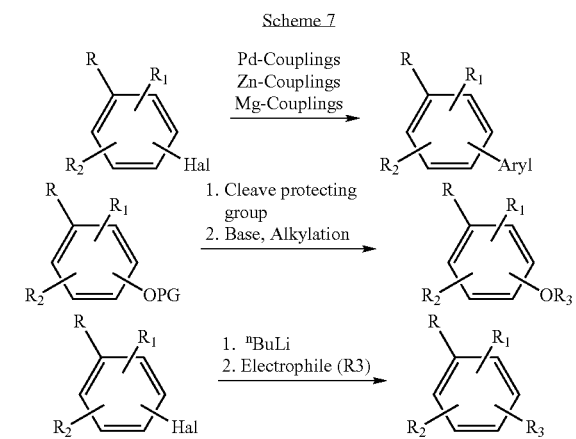

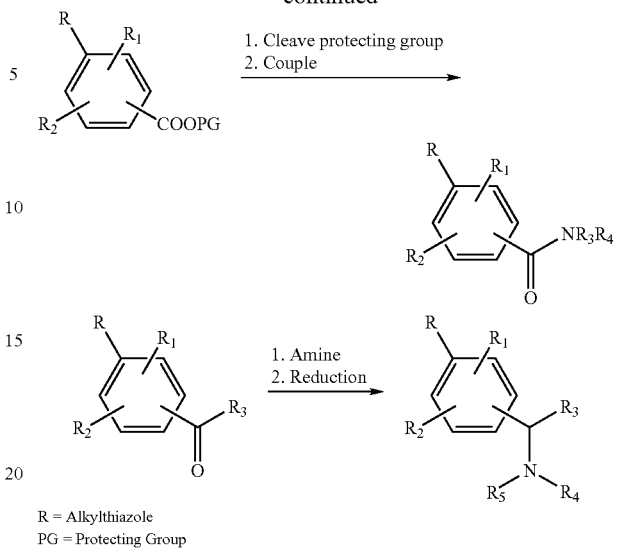

R = Alkylthiazole
PG = Protecting Group

High Speed Parallel Synthesis and Purification Technology

Compounds were synthesized either in glass tubes, 96 well plates (plastic or glass) or traditional flasks. The solvents were evaporated. The crude material was then dissolved in 1:1 methanol/DMSO and the desired product purified by reversed phase high performance liquid chromatography (HPLC) using an acetonitrile/water gradient and $C_{18}$ stationary phase. Filtrations prior to injection onto the high performance liquid chromatography mass spectrometer (HPLC/MS) system were done when necessary. The masses in the effluent were observed in real-time (via a spliter which diverts 1%) of the solvent stream into the PESCIEX API150EX mass spectrometer.

When the desired mass was observed a three way valve switched from waste to a fraction collector, where the products where isolated in tared tubes. The solvent was evaporated and the compounds were submitted for biological testing (see L. Zeng, X. Wang, T, Wang and D. B. Kassel, Combinatorial Chemistry & High Throughput Screening, 1998, 1, 101-111 and L. Zeng, L. Burton, K. Yung, B. Shushan, D. B. Kassel, J. Chromatogr. A, 1998, 794, 1-13)

Analytical Chemistry

Nuclear Magnetic Resonance Spectra ($^1$H-NMR) were obtained with a 300 MHz Varian Instrument. Coupling constants are expressed in Hertz (Hz). The chemical shifts are expressed in parts per million (ppm). The following abbreviations are utilized: s=singlet; m=multiplet; d=doublet; t=triplet; and q=quartet.

Synthesis of Cyclopropylnitrile Intermediates 1-(2-Chloro-6-fluoro-phenyl)-cyclopropanecarbonitrile To 2-chloro-5-fluoro-acetonitrile (5 g, 30 mmol) were added (134 mg, 0.72 mmol) of benzyltriethylammonium chloride and 5.9 mL (71 mmol) of 1-bromo-2-chloroethane. The mixture was warmed to 70° C. and then 23 mL (288 mmol) of 50% aqueous NaOH were added dropwise. The reaction was then stirred vigorously at 70° C. for 24 h and monitored by NMR. When conversion was complete, the reaction was cooled and partitioned between toluene and water. The organic solution was washed with brine, dried (magnesium sulfate), and concentrated in vacuo. Yield: 5.7 g (100%). $^1$H NMR (300 MHz, CDCl3), ••1.51 (m, cyclopropyl, 2H), 1.74 (s, CH$_2$, 4H), 1.94 (m, cyclopropyl, 2H), 4.06 (s, OCH$_3$, 3H), 7.25 (m, Ar, 4H).

2-{1-[4(2-Chloro-4-methoxy-5-methyl-phenyl)-5-methyl-thiazol-2-yl]-cyclopropyl}-3-methoxy-pyridine To 2-bromo-3-methoxy pyridine (1.7 g, 8.9 mmol) (obtained by treatment of 2-bromo-3-pyridinol with MeI) in 5.3 mL of toluene were added 2.4 mL (32 mmol) of cyclopropylcyanide and 27 mL (54 mmol) of a 0.5 M solution of potassium hexamethyldisilazide (KHMDS) in toluene. The mixture was stirred at room temperature for 8 h. The reaction was monitored by TLC and the product was purified by chromatography using ethyl acetate/hexane. Yield: 300 mg (20%). $^1$H NMR (300 MHz, CDCl3), ••1.81 (dd, cyclopropyl, 2H), 1.97 (dd, cyclopropyl, 2H), 2.25 (s, CH3, 3H), 2.3 (s, CH3, 3H), 3.92 (s, OCH3, 3H), 4.04 (s, OCH3, 3H), 6.93 (s, Ar, 1H), 7.35 (s, Ar, 1H), 7.7 (d, Ar, 2H), 8.56 (t, Ar, 1H)

Synthesis of Thioamide Intermediates 1-(2-Chloro-6-fluoro-phenyl)cyclopropane carbothioic acid amide 1-(2-Chloro-6-fluoro-phenyl)-cyclopropanecarbonitrile (5.7 g, 29 mmol) was dissolved in anhydrous ethanol followed by 4.1 mL (29.4 mmol) of triethylamine (TEA). Toluene was added to make a homogeneous solution. Hydrogen sulfide was bubbled through the reaction at room temperature for 1.5 h. The reaction was then sealed and stirred overnight at room temperature. Nitrogen was then bubbled through the solution for 2-3 hours, running the exhaust through gas-wash bottles filled with bleach. The reaction was concentrated in vacuo with the solvent trap on the rotary evaporator containing bleach solution. Redilution and concentration with hexane removed trace hydrogen sulfide. The product was triturated with hexane giving a yellowish solid. Yield: 5.5 g (83%) [MH]$^+$ 230.2, 232.2.

A. Synthesis of Aromatic α-haloketones

4-Chloro-2-methoxy-1-methyl-benzene

Commercially available 2-chloro-5-methylphenol (19.8 g, 70 mmol) was dissolved in 450 ml acetone. Potassium carbonate (28.9 g, 209 mmol) was added, followed by iodomethane (29.7 g, 209 mmol), and the mixture was refluxed overnight with vigorous stirring. The mixture was then filtered and concentrated in vacuo. The residue was dissolved in ethyl acetate, washed with water, dried with sodium sulfate, and concentrated giving 8.5 g 4-Chloro-2-methoxy-1-methyl-benzene (100%). $^1$H NMR (300 MHz, CDCl$_3$) •2.28 (s, CH$_3$, 3H), 3.92 (s, —OCH$_3$, 3H), 6.91 (d, Ar, 1H, J=2.0 Hz), 6.95 (dd, Ar, 1H, J=8.0, 2.0 Hz), 7.14 (m, Ar, 1H).

1-(2-Chloro-4-methoxy-5-methly-phenyl)-propan-1-one

In a three neck round bottom flask equipped with a reflux condenser and stir bar under N$_2$ atmosphere was added finely pulverized aluminum trichloride (8.7 g, 65.2 mmol) to dichloroethane (22 mL). The solution was chilled to 0° C. Propionyl chloride was added dropwise 4.9 mL (57 mmol) and the mixture was stirred vigorously for 10 min. 4-Chloro-2-methoxy-1-methyl-benzene (8.5 g, 54.3 mmol) was then added dropwise with cooling to maintain internal solution temperature below 20° C. For less reactive aromatic rings the arene itself was used as solvent. The mixture was stirred for one hour with gradual warming to room temperature, then heated to 50° C. overnight. When starting material was not visible by TLC the reaction was cooled to room temperature. The reaction was quenched by pouring into ice and the layers separated in a separatory funnel. The aqueous phase was extracted once with chloroform. The combined organic layers were washed with 10 N HCl, water, aqueous NaHCO$_3$ (saturated) then dried (sodium sulfate), and concentrated in vacuo. The product was then purified by chromatography on silica using an ethyl acetate/hexane gradient. Yield: 5.41 g white crystals (51%). $^1$H NMR (300 MHz, CDCl$_3$) •1.28 (t, CH$_3$, 3H, J=7.0 Hz), 2.27 (s, CH$_3$, 3H), 3.06 (q, CH$_2$, 2H, J=7.0 Hz) 3.95 (s, —OCH$_3$, 3 H), 6.91 (s, Ar, 1H, ), 6.95 (s, Ar, 1H), 7.50 (s, Ar, 1H).

1-(2-Chloro-4-methoxy-5-methyl-phenyl)-propan-1-one to 2-Bromo-1-(2-chloro-4-methoxy-5-methly-phenyl)-propan-1-one 1-(2-Chloro-4-methoxy-5-methyl-phenyl)-propan-1-one (5.4 g, 25 mmol) was dissolved in chloroform (25 ml). Bromine (1.3 mL, 25.0 mmol) was then added dropwise via addition funnel. The reaction was monitored by TLC using ethyl acetate/hexane mixtures until starting material was consumed (8 h). The reaction was quenched by addition of 5%) aqueous sodium bisulfite (1 volume equivalent relative to chloroform) and the mixture stirred vigorously for 15 min. The mixture was then diluted with an additional volume equivalent of chloroform, partitioned, and the organic solution washed with 5%) aqueous bisulfite, brine, dried (sodium sulfate), then concentrated in vacuo. Purification on silica using an ethyl acetate/hexane gradient resulting in a yellow oil. Yield: 7.4 g (99%). $^1$H NMR (300 MHz, CDCl$_3$) •1.97 (d, CH$_3$, 3H, J=6.8 Hz), 2.28 (s, CH$_3$, 3H), 3.96 (s, —OCH$_3$, 3H), 5.47 (q, CH, 1H, J=6.8 Hz), 6.91 (s, Ar, 1H,), 6.92 (s, Ar, 1H), 7.50 (s, Ar, 1H).

B. Synthesis of Heteroaromatic α-haloketones 1-(2,6-dimethl-pyridine-3-yl)-propan-1-one 3-bromo-2,6-dimethyl-pyridine, (3.72 g, 20 mmol) were dissolved in 40 mL diethylether at −78° C. and treated with 10 mL of n-butyllithium (20 mmol) as a 2 M commercial solution in hexane. After stirring for 0.5 h, propionitrile (1.21 g, 22 mmol) was added and the mixture allowed to slowly warm to room temperature while stirring overnight. The mixture was then poured into water (0.5 volume equivalents relative to ether) and the mixture partitioned. The aqueous solution was extracted with ethyl acetate and the combined organic layers washed with water, dried with sodium sulfate, and concentrated in vacuo. Chromatography on silica using an ethyl acetate/hexane gradient gave the final product. Yield: 0.3 g (9%) $^1$H NMR (300 MHz, CDCl$_3$), •1.18 (t, CH$_3$, 3H), 2.56 (s, CH$_3$, 3H), 2.68 (s, —CH$_3$, 3H), 2.86 (q, CH$_2$, 2H), 7.04 (d, Ar, 1H,), 7.8 (d, Ar, 1H).

2-Bromo-1-(2,6-dimethyl-pyridine-3-yl)-propan-1-one

To a solution 1-(2,6-dimethl-pyridine-3-yl)-propan-1-one (0.3 g, 1.8 mmol) in 30% by weight solution of hydrogen bromide in acetic acid (3 ml) was added dropwise (0.29 g, 1.8 mmol) of Bromine. The reaction was allowed to warm to room temperature with stirring for 2h. The mixture was then concentrated in vacuo and the resulting crude material neutralized using saturated sodium carbonate solution. The mixture was extracted twice with dichloromethane and the combined organic layers were washed with water and brine, dried over sodium sulfate and concentrated in vacuo. Yield: 400 mg (92%). $^1$H NMR (300 MHz, CDCl$_3$), •1.88 (d, CH$_3$, 3H), 2.64 (s, CH$_3$, 3H), 2.76 (s, CH$_3$, 3H), 5.12 (q, CH, 1H), 7.14 (d, Ar, 1 H,), 7.93 (d, Ar, 1 H).

Synthesis of Intermediates for C5-modified Thiazoles

4-(2,4-Dichloro-phenyl)-2-[1-(2-methoxy-phenyl)-cyclopropyl]-thiazole

The procedures outlined for using propiophenone precursors were applied without modification to the synthesis of the corresponding acetophenone analogs.

Representative compounds prepared using the general Schemes 1-6 are listed in the following Tables 1-5.

TABLE 1

Substituted 5-methylthiazoles

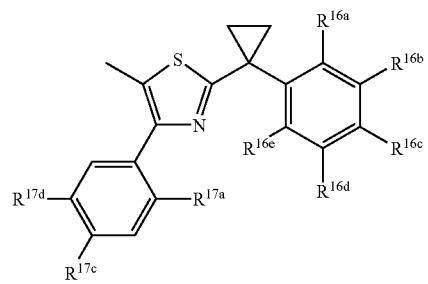

| Ex. No. | R16a | R16b | R16c | R16d | R16e | R17a | R17c | R17d |
|---|---|---|---|---|---|---|---|---|
| 1 | Bn | H | H | H | H | OMe | OMe | H |
| 2 | p-CN-Bn | H | H | H | H | OMe | Ome | H |
| 3 | CCH | H | H | H | H | Cl | Cl | H |
| 4 | CCH | H | H | H | H | H | CF$_3$ | H |
| 5 | CCH | H | H | H | H | H | OMe | F |
| 6 | CCH | H | H | H | H | H | OMe | H |
| 7 | CF$_3$ | H | H | H | H | Cl | Cl | H |
| 8 | CF$_3$ | H | H | H | H | Cl | H | H |
| 9 | CF$_3$ | H | H | H | H | Cl | OMe | H |
| 10 | CF$_3$ | H | H | H | H | Cl | OMe | Me |
| 11 | CF$_3$ | H | H | H | H | F | CF$_3$ | H |
| 12 | CF$_3$ | H | H | H | H | H | CF$_3$ | H |
| 13 | CF$_3$ | H | H | H | H | H | OMe | H |
| 14 | CF$_3$ | H | H | H | H | OMe | OMe | Br |
| 15 | CF$_3$ | H | H | H | H | OMe | OMe | H |
| 16 | Cl | Cl | H | H | H | Cl | Cl | H |
| 17 | Cl | Cl | H | H | H | H | OMe | H |
| 18 | Cl | H | Cl | H | H | Cl | Cl | H |
| 19 | Cl | H | Cl | H | H | Cl | H | H |
| 20 | Cl | H | Cl | H | H | Cl | OMe | Me |
| 21 | Cl | H | Cl | H | H | F | F | H |
| 22 | Cl | H | Cl | H | H | H | CF$_3$ | H |
| 23 | Cl | H | Cl | H | H | H | Cl | H |
| 24 | Cl | H | Cl | H | H | H | Me | Cl |
| 25 | Cl | H | Cl | H | H | H | Me | H |
| 26 | Cl | H | Cl | H | H | H | NMe$_2$ | Br |
| 27 | Cl | H | Cl | H | H | H | OCHF$_2$ | H |
| 28 | Cl | H | Cl | H | H | H | OEt | H |
| 29 | Cl | H | Cl | H | H | H | OMe | H |
| 30 | Cl | H | Cl | H | H | H | SMe | H |
| 31 | Cl | H | Cl | H | H | OMe | OMe | Br |
| 32 | Cl | H | Cl | H | H | OMe | OMe | H |
| 33 | Cl | H | F | H | H | Cl | Cl | H |
| 34 | Cl | H | F | H | H | Cl | OMe | H |
| 35 | Cl | H | F | H | H | F | CF$_3$ | H |
| 36 | Cl | H | F | H | H | OMe | OMe | H |
| 37 | Cl | H | H | H | H | Cl | Cl | H |
| 38 | Cl | H | H | H | Cl | Cl | Cl | H |
| 39 | Cl | H | H | H | F | Cl | Cl | H |
| 40 | Cl | H | H | H | Cl | Cl | H | H |
| 41 | Cl | H | H | H | H | Cl | OMe | Me |

TABLE 1-continued

Substituted 5-methylthiazoles

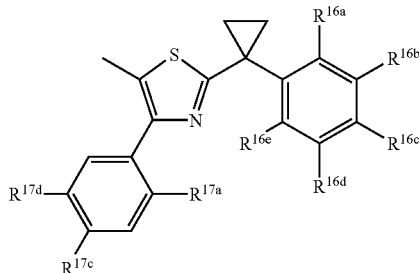

| Ex. No. | R16a | R16b | R16c | R16d | R16e | R17a | R17c | R17d |
|---|---|---|---|---|---|---|---|---|
| 42 | Cl | H | H | H | F | Cl | OMe | Me |
| 43 | Cl | H | H | H | Cl | Cl | OMe | Me |
| 44 | Cl | H | H | H | Cl | H | $CF_3$ | H |
| 45 | Cl | H | H | H | H | H | Cl | H |
| 46 | Cl | H | H | H | H | H | Me | H |
| 47 | Cl | H | H | H | H | H | OMe | H |
| 48 | Cl | H | H | H | Cl | H | OMe | H |
| 49 | Cl | H | H | H | F | OMe | OMe | H |
| 50 | CN | H | H | H | H | Cl | Cl | H |
| 51 | CN | H | H | H | H | Cl | OMe | Me |
| 52 | CN | H | H | H | H | H | OMe | H |
| 53 | CN | H | H | H | H | OMe | OMe | H |
| 54 | 5-tetrazolyl | H | H | H | H | OMe | OMe | H |
| 55 | COOMe | H | H | H | H | H | OMe | H |
| 56 | F | F | H | H | H | Cl | Cl | H |
| 57 | F | F | H | H | H | H | OMe | H |
| 58 | F | H | H | F | H | Cl | Cl | H |
| 59 | F | H | H | F | H | H | OMe | H |
| 60 | F | H | H | F | H | H | Cl | H |
| 61 | F | H | H | F | H | OMe | OMe | H |
| 62 | F | H | H | H | Cl | H | Cl | H |
| 63 | F | H | H | H | Cl | H | OMe | H |
| 64 | F | H | H | H | F | Cl | Cl | H |
| 65 | F | H | H | H | F | H | OMe | H |
| 66 | F | H | H | H | H | Cl | Cl | H |
| 67 | F | H | H | H | H | H | OMe | H |
| 68 | F | H | H | H | H | H | OMe | F |
| 69 | H | $CF_3$ | H | H | H | Cl | Cl | H |
| 70 | H | Cl | H | H | H | Cl | Cl | H |
| 71 | H | Cl | H | H | H | H | Cl | H |
| 72 | H | Cl | H | H | H | H | Cl | H |
| 73 | H | Cl | H | H | H | H | Me | H |
| 74 | H | F | H | F | H | H | OMe | H |
| 75 | H | F | H | H | H | H | OMe | H |
| 76 | H | H | Cl | H | H | Cl | Cl | H |
| 77 | H | H | Cl | H | H | Cl | OMe | Me |
| 78 | H | H | Cl | H | H | H | OEt | H |
| 79 | H | H | F | H | H | Cl | Cl | H |
| 80 | H | H | F | H | H | Cl | OMe | H |
| 81 | H | H | F | H | H | Cl | OMe | Me |
| 82 | H | H | F | H | H | OMe | OMe | H |
| 83 | H | H | H | H | H | Cl | Cl | H |
| 84 | H | H | H | H | H | Cl | OMe | Me |
| 85 | H | H | H | H | H | F | H | H |
| 86 | H | H | H | H | H | H | Et | H |
| 87 | H | H | H | H | H | H | OMe | H |
| 88 | H | H | H | H | H | OMe | OMe | H |
| 89 | H | H | Me | H | H | Cl | Cl | H |
| 90 | H | H | OMe | H | H | Cl | Cl | H |
| 91 | H | H | OMe | H | H | H | Me | H |
| 92 | H | H | OMe | H | H | H | SMe | H |
| 93 | H | Me | F | H | H | H | OMe | H |
| 94 | H | OMe | H | H | H | Cl | Cl | H |
| 95 | H | OMe | H | H | H | H | OMe | H |
| 96 | H | OMe | OMe | H | H | Cl | Cl | H |
| 97 | I | H | H | H | H | Cl | OMe | Me |
| 98 | I | H | H | H | H | H | OMe | H |
| 99 | I | H | H | H | H | OMe | OMe | H |
| 100 | Me | H | F | H | H | OMe | OMe | H |

TABLE 1-continued

Substituted 5-methylthiazoles

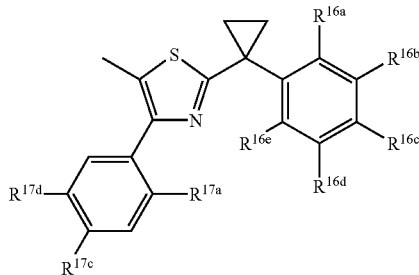

| Ex. No. | R16a | R16b | R16c | R16d | R16e | R17a | R17c | R17d |
|---|---|---|---|---|---|---|---|---|
| 101 | Me | H | H | F | H | H | OMe | H |
| 102 | Me | H | H | H | F | Me | Me | H |
| 103 | Me | H | H | H | H | OMe | OMe | H |
| 104 | OBn | H | H | H | H | Cl | OMe | Me |
| 105 | OBn | H | H | H | H | H | OMe | H |
| 106 | OC$_2$H$_4$OMe | H | H | H | H | OMe | OMe | H |
| 107 | OCF$_3$ | H | H | H | H | Cl | Cl | H |
| 108 | OCF$_3$ | H | H | H | H | Cl | OMe | H |
| 109 | OCF$_3$ | H | H | H | H | Cl | OMe | Me |
| 110 | OCF$_3$ | H | H | H | H | H | Cl | H |
| 111 | OCF$_3$ | H | H | H | H | H | OMe | H |
| 112 | OCF$_3$ | H | H | H | H | Me | Me | H |
| 113 | OCH$_2$CCH | H | H | H | H | OMe | OMe | H |
| 114 | OCH$_2$CHCH$_2$ | H | H | H | H | OMe | OMe | H |
| 115 | OCH$_2$CN | H | H | H | H | Cl | OMe | Me |
| 116 | OCH$_2$CN | H | H | H | H | OMe | OMe | H |
| 117 | OCH$_2$CO$_2$Me | H | H | H | H | Cl | OMe | Me |
| 118 | OCH(Me)COMe | H | H | H | H | OMe | OMe | H |
| 119 | OCH(Me)COOEt | H | H | H | H | OMe | OMe | H |
| 120 | OCH(Me)COOMe | H | H | H | H | OMe | OMe | H |
| 121 | OEt | H | H | H | H | Cl | Cl | H |
| 122 | OEt | H | H | H | H | Cl | OMe | H |
| 123 | OEt | H | H | H | H | H | OMe | H |
| 124 | OEt | H | H | H | H | H | Cl | H |
| 125 | OEt | H | H | H | H | OMe | OMe | H |
| 126 | OH | H | H | H | H | Cl | OMe | Me |
| 127 | OMe | H | F | H | H | OMe | OMe | H |
| 128 | OMe | H | H | Br | H | Cl | Cl | H |
| 129 | OMe | H | H | Br | H | Cl | OMe | H |
| 130 | OMe | H | H | Br | H | Cl | OMe | Me |
| 131 | OMe | H | H | Br | H | H | OMe | H |
| 132 | OMe | H | H | Br | H | OMe | OMe | H |
| 133 | OMe | H | H | CH$_2$COMe | H | Cl | OMe | Me |
| 134 | OMe | H | H | CH(OH)Me | H | Cl | OMe | Me |
| 135 | OMe | H | H | CH(OH)CMe$_3$ | H | Cl | OMe | Me |
| 136 | OMe | H | H | CN | H | Cl | Cl | H |
| 137 | OMe | H | H | CN | H | Cl | OMe | Me |
| 138 | OMe | H | H | COMe | H | Cl | OMe | Me |
| 139 | OMe | H | H | CONMe$_2$ | H | Cl | OMe | Me |
| 140 | OMe | H | H | F | F | H | OMe | H |
| 141 | OMe | H | H | F | H | OMe | OMe | H |
| 142 | OMe | H | H | H | H | CF$_3$ | CF$_3$ | H |
| 143 | OMe | H | H | H | H | CH$_2$OH | OMe | H |
| 144 | OMe | H | H | H | H | Cl | Cl | H |
| 145 | OMe | H | H | H | H | Cl | H | H |
| 146 | OMe | H | H | H | H | Cl | OMe | H |
| 147 | OMe | H | H | H | H | CN | OMe | H |
| 148 | OMe | H | H | H | H | CO$_2$Me | OMe | H |
| 149 | OMe | H | H | H | H | F | CF$_3$ | H |
| 150 | OMe | H | H | H | H | H | CF$_3$ | H |
| 151 | OMe | H | H | H | H | H | Cl | H |
| 152 | OMe | H | H | H | H | H | Me | H |
| 153 | OMe | H | H | H | H | H | OMe | F |
| 154 | OMe | H | H | H | H | H | OMe | H |
| 155 | OMe | H | H | H | H | I | OMe | H |
| 156 | OMe | H | H | H | H | Me | Me | H |
| 157 | OMe | H | H | H | H | OMe | OMe | H |
| 158 | OMe | H | H | Me | H | Cl | Cl | H |
| 159 | OMe | OMe | H | H | H | Cl | Cl | H |

TABLE 1-continued

Substituted 5-methylthiazoles

| Ex. No. | R16a | R16b | R16c | R16d | R16e | R17a | R17c | R17d |
|---|---|---|---|---|---|---|---|---|
| 160 | OMe | OMe | H | H | H | Cl | OMe | H |
| 161 | OMe | OMe | H | H | H | H | Cl | H |
| 162 | OMe | OMe | H | H | H | H | OMe | H |
| 163 | OMe | OMe | H | H | H | OMe | OMe | H |
| 164 | OPh | H | H | H | H | Cl | Cl | H |
| 165 | OPh | H | H | H | H | Cl | OMe | H |
| 166 | OPh | H | H | H | H | Cl | OMe | Me |
| 167 | OPh | H | H | H | H | H | Cl | H |
| 168 | OPh | H | H | H | H | H | OMe | H |
| 169 | OPh | H | H | H | H | OMe | OMe | H |
| 170 | Ph | H | H | H | H | Cl | Cl | H |
| 171 | Ph | H | H | H | H | H | OMe | H |
| 172 | $SCF_3$ | H | H | H | H | Cl | Cl | H |
| 173 | $SCF_3$ | H | H | H | H | Cl | OMe | Me |
| 174 | $SCF_3$ | H | H | H | H | H | Cl | H |
| 175 | $SCF_3$ | H | H | H | H | OMe | OMe | H |
| 176 | SMe | H | H | H | H | OMe | OMe | H |

TABLE 2

C5-Substituted thiazoles

| Ex. No. | R16a | R16c | R1 | R17a | R17c | R17d |
|---|---|---|---|---|---|---|
| 177 | $CF_3$ | H | Br | OMe | OMe | H |
| 178 | $CF_3$ | H | $CH_2OH$ | H | Cl | H |
| 179 | $CF_3$ | H | CHO | OMe | OMe | H |
| 180 | $CF_3$ | H | CH(OH)Me | OMe | OMe | H |
| 181 | $CF_3$ | H | CN | OMe | OMe | H |
| 182 | $CF_3$ | H | COMe | OMe | OMe | H |
| 183 | $CF_3$ | H | I | OMe | OMe | H |
| 184 | $CF_3$ | H | $SCF_3$ | OMe | OMe | H |
| 185 | Cl | Cl | $CH_2OH$ | Cl | Cl | H |
| 186 | H | F | CHO | OMe | OMe | H |
| 187 | H | F | Cocyclopropyl | OMe | OMe | H |
| 188 | $OCF_3$ | H | CHO | Me | Me | H |
| 189 | $OCF_3$ | H | CH(OH)Me | Cl | OMe | Me |
| 190 | OEt | H | CH(OH)Me | OMe | OMe | H |
| 191 | OEt | H | I | OMe | OMe | H |
| 192 | OMe | H | Br | Cl | Cl | H |
| 193 | OMe | H | Br | Me | Me | H |
| 194 | OMe | H | $CF_3$ | Cl | Cl | H |
| 195 | OMe | H | $CH_2CHO$ | Cl | Cl | H |
| 196 | OMe | H | $CH_2OH$ | Cl | Cl | H |
| 197 | OMe | H | $CH_2OH$ | H | Cl | H |
| 198 | OMe | H | $CH_2OH$ | H | OMe | H |

TABLE 2-continued

C5-Substituted thiazoles

| Ex. No. | R16a | R16c | R1 | R17a | R17c | R17d |
|---|---|---|---|---|---|---|
| 199 | OMe | H | $CH_2OH$ | OMe | OMe | H |
| 200 | OMe | H | $CHF_2$ | Cl | Cl | H |
| 201 | OMe | H | CHO | Cl | Cl | H |
| 202 | OMe | H | CHO | Cl | OMe | Me |
| 203 | OMe | H | CHO | Me | Me | H |
| 204 | OMe | H | CHO | OMe | OMe | H |
| 205 | OMe | H | CH(OH)Me | $CF_3$ | $CF_3$ | H |
| 206 | OMe | H | CH(OH)Me | Cl | Cl | H |
| 207 | OMe | H | CH(OH)Me | Cl | OMe | Me |
| 208 | OMe | H | CH(OH)Me | Me | Me | H |
| 209 | OMe | H | CH(OH)Me | OMe | OMe | H |
| 210 | OMe | H | COMe | Cl | Cl | H |
| 211 | OMe | H | COMe | Cl | OMe | Me |
| 212 | OMe | H | COOMe | Cl | Cl | H |
| 213 | OMe | H | I | $CF_3$ | $CF_3$ | H |
| 214 | OMe | H | I | Cl | Cl | H |
| 215 | OMe | H | I | Cl | OMe | Me |
| 216 | OMe | H | I | Me | Me | H |
| 217 | OMe | H | I | OMe | OMe | H |
| 218 | OMe | H | $NH_2$ | Cl | Cl | H |
| 219 | OMe | H | $NO_2$ | Cl | Cl | H |
| 220 | OMe | H | SMe | Cl | Cl | H |
| 221 | OMe | H | SMe | Me | Me | H |

TABLE 3

Miscellaneous 5-methylthiazoles

| Ex. No. | R16a | R16b | R16c | R16d | R16e | R17a | R17c | R17e |
|---|---|---|---|---|---|---|---|---|
| 222 | $CF_3$ | H | H | H | H | Me | Me | Me |
| 223 | Cl | H | F | H | H | Me | Me | Me |
| 224 | F | H | H | H | Cl | Me | Me | Me |
| 225 | H | H | H | H | H | F | H | $CF_3$ |
| 226 | OMe | H | H | H | H | F | H | $CF_3$ |
| 227 | OMe | H | H | H | H | Me | Me | Me |

TABLE 4

Heteroaryl substituted 5-methylthiazoles

| Ex. No | Ar1 | Ar2 |
|---|---|---|
| 228 | 2-methyl-3-methylthiophene (Me, S, Me) | 2,4-dimethoxyphenyl (OMe, OMe) |
| 229 | 2-methoxyphenyl (OMe) | 2,6-dimethylpyridine (Me, N, Me) |
| 230 | 2,3-dimethylpyridine (Me, Me, N) | 3-bromo-4-methoxyphenyl (Br, OMe) |
| 231 | 2,3-dimethylpyridine (Me, Me, N) | 2,4-dichlorophenyl (Cl, Cl) |
| 232 | 2,3-dimethylpyridine (Me, Me, N) | 4-trifluoromethylphenyl ($CF_3$) |
| 233 | 3-chloro-2-methyl-5-trifluoromethylpyridine (Cl, Me, N, $CF_3$) | 3-bromo-4-methoxyphenyl (Br, OMe) |

TABLE 4-continued

Heteroaryl substituted 5-methylthiazoles

| Ex. No | Ar1 | Ar2 |
|---|---|---|
| 234 | 3-Cl, 2-Me, 5-CF₃-pyridin-yl | 2,4-dichlorophenyl |
| 235 | 2-Me, 3-Me-pyridin-yl | 4-methoxyphenyl |
| 236 | 2-Me, 3-Me-pyridin-yl | 4-chlorophenyl |
| 237 | 2-Me, 3-Me-pyridin-yl | 2,4-dichlorophenyl |
| 238 | 2-methyl, 3-methoxyphenyl | 2-methyl, 5-methylpyridinyl |
| 239 | 2-methyl, 3-OCF₃-phenyl | 2-methyl, 5-methylpyridinyl |
| 240 | 2,6-dichloro, 3-methylphenyl | 5-methyl, 2-methoxypyridinyl |
| 241 | 2,6-dichloro, 3-methylphenyl | 2,6-dimethyl, 3-methylpyridinyl |
| 242 | 2-methyl, 3-CF₃-phenyl | 2,6-dimethyl, 3-methylpyridinyl |
| 243 | 2-methyl, 3-OCF₃-phenyl | 2,6-dimethyl, 3-methylpyridinyl |
| 244 | 2-methyl, 3-methoxypyridinyl | 2,5-dimethyl, 4-chloro, 5-methoxyphenyl |
| 245 | 2-methyl, 3-methoxy, 5-bromophenyl | 2,6-dimethyl, 3-methylpyridinyl |

TABLE 5

Oxazoles

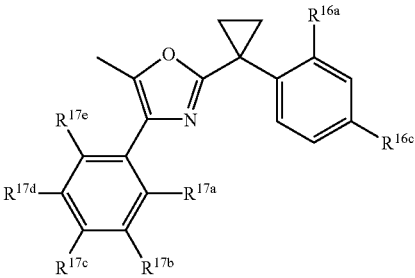

| Ex. No | R16a | R16c | R17a | R17b | R17c | R17d | R17e |
|---|---|---|---|---|---|---|---|
| 246 | Cl | Cl | H | CF$_3$ | F | H | H |
| 247 | Cl | Cl | Cl | H | Cl | H | H |
| 248 | Cl | Cl | CF$_3$ | H | H | H | F |
| 249 | OMe | H | Cl | H | Cl | H | H |
| 250 | Cl | Cl | Cl | H | OMe | Me | H |

EXAMPLES

Example 42

2-[1-(2-Chloro-6-fluoro-phenyl)-cyclopropyl]-4-(2-chloro-4-methoxy-5-methly-phenyl)-5-methyl-thiazole 2-Bromo-1-(2-chloro-4-methoxy-5-methly-phenyl)-propan-1-one (254 mg, 0.87 mmol) and 1-(2-Chloro-6-fluoro-phenyl) cyclopropane carbothioic acid amide (200 mg, 0.87 mmol) were dissolved in dimethlyformamide (DMF) (2.9 mL). The reaction was heated with stirring to 80° C. overnight. The mixture was then cooled, diluted with ethyl acetate and washed three times with water and once with brine. The organic layer was separated, dried with sodium sulfate and concentrated in vacuo. The crude product was then chromatographed on silica using an ethyl acetate/hexane gradient resulting in a pale green-yellow solid. Yield: 110 mg (18%). [MH]$^+$422.0. $^1$H NMR (300 MHz, CDCl$_3$) •1.54 (m, cyclopropyl, 2H), 2.11 (m, cyclopropyl, 2H), 2.27 (s, CH$_3$, 3H), 2.28 (s, CH$_3$, 3H), 3.93 (s, —OCH$_3$, 3H), 6.97 (s, Ar, 1H), 7.15 (m, Ar, 1H), 7.35 (s, Ar, 1H), 7.37 (m, Ar, 2H).

Example 229

3-{2-[1-(2-Methoxy-phenyl)-cyclopropyl]-5-methyl-thiaol-4-yl}-2,6-dimethyl-pyridine The title compound was prepared using the same procedure as described for Example 42. Yield: 3 mg (4%). [MH]$^+$351.4.

Example 246

2-{1-[4-(2-Chloro-4-methoxy-5-methyl-phenyl)-5-methyl-thiazol-2-yl]cyclopropyl}-3-methoxy-pyridine The title compound was prepared from (25.3 mg, 0.1 mmol) of the thioamide and (29 mg, 0.1 mmol) of the α-bromoketone using the same procedure as described for Example 42. Yield: 10.6 mg, (27%). [MH]$^+$ 401.2, 403.0.

Example 210

1-{4-(2,4-Dichloro-phenyl)-2-[1-(2-methoxy-phenyl)-cyclopropyl]-thiazol-5-yl}-ethanone 4-(2,4-Dichloro-phenyl)-2-[1-(2-methoxy-phenyl)-cyclopropyl]-thiazole (30 mg, 0.079 mmol) was dissolved in 1 mL of dry THF and the solution was cooled to −78° C. N-butyllithium (0.044 mL, 0.088 mmol) was added dropwise as a commercial 2M solution in pentane and the reaction stirred for 30 min at −78° C. Acetylchloride (0.056 mL, 0.79 mmol) was added as a neat liquid and the reaction warmed to room temperature with stirring over 1h. Water (1 volume equivalent relative to THF) was added and the THF removed in vacuo. The crude material was then dissolved in 1:1 methanol/DMSO (2 volume equivalents relative to THF) and the desired product purified by reversed phase HPLC/MS using an acetonitrile/water gradient and C$_{18}$ stationary phase. Yield: 4.4 mg (14%). [MH]$^+$ 418.2, 420.2.

Example 206

1-{4-(2,4-Dichloro-phenyl)-2-[1-(2-methoxy-phenyl)-cycloprpoyl]-thiazole-5-yl}-ethanol The title compound was prepared by the same procedure as described for Example 210 using 0.044 mL (0.79 mmol) of acetaldehyde as electrophile. Yield: 7.4 mg (23%). [MH]$^+$ 420.2, 422.4.

Example 214

1-{4-(2,4-Dichloro-phenyl)-5-iodo-2-[1-(2-methoxy-phenyl)-cyclopropyl]-thiazole

The title compound was prepared by the same procedure as described for Example 210 using 200 mg (0.79 mmol) of iodine as electrophile. Yield: 11.6 mg (30%). [MH]$^+$ 502.0, 503.8.

Example 219

4-(2,4-Dichloro-phenyl)-2-[1-(2-methoxy-phenyl)-cyclopropyl]-5-nitro-thiazole

The title compound was prepared by the same procedure as described for Example 210 using 105 mg (0.79 mmol) of nitronium terafluoroborate as electrophile. Yield: 1.2 mg (4%). [MH]$^+$ 421.8, 424.2.

Example 220

4-(2,4-Dichloro-phenyl)-2-[1-(2-methoxy-phenyl)-cyclopropyl]-5-methylsulfanyl-thiazole The title compound was prepared by the same procedure as described for Example 210 using 0.067 mL (0.79 mmol) of methyldisulfide as electrophile. Yield: 11.9 mg (36%), [MH]$^+$ 422.0, 424.0.

Example 155

4-(2-Iodo-4-methoxy-phenyl)-2-[1-(2-methoxy-phenyl)-cyclopropyl]-5-methyl-thiazole 2-Bromo-1-(2-iodo-4-methoxy-phenyl)-propan-1-one was synthesized from commercially available 3-iodoanisole via Friedel-Crafts acylation and bromination (vide supra). The 2-Bromo-1-(2-iodo-4-methoxy-phenyl)-propan-1-one (2.6 g, 7.0 mmol) was carried into the Hantzsch synthesis with 1-(2-Methoxy-phenyl)-cyclopropanecarbothioic acid amide (7.0 mmol, 1.45 g). The resulting iodoaryl thiazole was purified by chromatography on silica using ethyl acetate/hexane gradient. Yield: 790 mg, oil, (24%). $[MH]^{30}$ 478.0.

Example 50

2-{1-[4-(2,4-Dichloro-phenyl)-5-methyl-thiazol-2-yl]-cyclopropyl}-benzonitrile

Tetrakis(triphenylphosphine) palladium(0) (47 mg, 0.41 mmol), copper (I) iodide 15.6 mg (0.082 mmol), finely pulverized potassium cyanide (56 mg, 0.86 mmol), and iodoaryl thiazole (Example 155) (200 mg, 0.41 mmol) were combined in a one-dram vial and placed under an atmosphere of nitrogen. Degassed acetonitrile (2.5 mL) was then added and the mixture stirred overnight at 75° C. The reaction was cooled, dissolved in ethyl acetate, and filtered through Celite. The solution was washed with water, brine, then dried with magnesium sulfate and concentrated in vacuo. The crude product was purified by HPLC/$SiO_2$ using a ethyl acetate/hexane gradient. Yield: 77 mg, (48%). $[MH]^+$ 395.2, 397.2.

Example 54

2-(2-{1-[4-(2,4-Dimethoxy-phenyl)-5-methyl-thiazol-2-yl]-cyclopropyl}-phenyl)-1H-tetrazole The 2-{1-[4-(2,4-Dichloro-phenyl)-5-methyl-thiazol-2-yl]-cyclopropyl}-benzonitrile (55 mg, 0.16 mmol) was combined with sodium azide (12 mg, 0.18 mmol) and placed under a nitrogen atmosphere. Xylene was added (0.6 mL) followed by tributyltin chloride (59 mg, 0.18 mmol). The reaction was heated to 130° C. with stirring for three days until complete by analytical LC/MS. The mixture was then cooled, diluted with toluene (1.2 mL) and hydrogen chloride added as a commercial 1 M solution in ether (1.8 mmol, 10 eq.). The reaction was stirred for 15 min and the resulting solid filtered, washed with toluene, and dissolved in 1:1 methanol/DMSO. The desired product was purified by reversed phase HPLC/MS using a (40-99%) acetonitrile/water gradient and $C_{18}$ stationary phase. Yield: 36 mg (53%). $[MH]^+$ 420.2, 392.4.

Example 138

1-(3-{1-[4-(2-Chloro-4-methoxy-5-methyl-phenyl)-5-methyl-thiazol -2-yl]-cyclopropyl}-4-methoxy-phenyl)-ethanone 2-([1-(5-Bromo-2-methoxy-phenyl)-cyclopropyl]-4-(4-methoxy-2,5-dimetyl-phenyl)-5-thiazole (20 mg, 0.04 mmol) was dissolved in 1 mL of dry THF and the solution was cooled to −78° C. N-butyllithium (0.025 mL, 0.05 mmol) was then added dropwise as a commercial 2 M solution in pentane and the reaction was warmed to −40° C. The reaction mixture was then cooled to −78° C. and 0.029 mL (0.41 mmol) of acetylchloride was added as a neat liquid. After the addition the reaction mixture was warmed to room temperature and stirred for 8h. Water (1 volume equivalent relative to THF) was added and the THF removed in vacuo. The crude material was then dissolved in 1:1 methanol/DMSO (2 volume equivalents relative to THF) and the desired product purified by reversed phase HPLC/MS using an acetonitrile/water gradient and $C_{18}$ stationary phase. 0.8 mg of product were obtained. Yield: 0.8 mg (5%),. $[MH]^+$ 442.2, 444.4.

Example 134

1-(3-{1-[4-(2-Chloro-4-methoxy-5-methyl-phenyl)-5-methyl-thiazol-2-yl]-cyclopropyl}-4-methoxy-phenyl)-ethanol The title compound was prepared using 2-([1-(5-Bromo-2-methoxy-phenyl)-cyclopropyl]-4-(4-methoxy-2,5-dimetyl-phenyl) -5-thiazole (20 mg, 0.041 mmol) and acetaldehyde as electophile (0.023 mL, 0.41 mmol) with the procedure described for Example 138. Yield: 1.6 mg (9%). $[MH]^+$ 444.4, 446.2.

Example 139

1-(3-{1-[4-(2-Chloro-4-methoxy-5-methyl-phenyl)-5-methyl-thiazol -2-yl]-cyclopropyl}-4-methoxy-N,N-dimethyl-benzamide The title compound was prepared by using using 2-([1-(5-Bromo-2-methoxy-phenyl)-cyclopropyl]-4-(4-methoxy-2,5-dimetyl-phenyl)-5-thiazole (20 mg, 0.041 mmol) and dimethylcarbarmylchloride as electrophile (0.03 mL, 0.41 mmol). Following the procedure described for Example 138. Yield: 1.4 mg (7%). $[MH]^+$ 471.4, 473.2.

Example 137

3-{1-[4-(2-Chloro-4-methoxy-5-methyl-phenyl)-5-methyl-thiazol -2-yl]-cyclopropyl}-4-methoxy-benzonitrile 5-Bromo-4-(2-chloro-4-methoxy-5-methyl-phenyl)-2-[1-(2-methoxy-phenyl)cyclopropyl]-thiazole (150 mg, 0.32 mmol) was placed in a reaction vessel, Zinc cyanide (185 mg, 1.57 mmol) and tetrakis(triphenylphosphine)palladium (0) (150 mg, 0.13 mmol) was added and the tube was sealed and flushed with nitrogen. Dry acetonitrile (5 ml) was added and the mixture was heated to 190° C. submitted to microwave irradiation for 10 min (Smith Workstation™, Personal Chemistry Inc.). The solid was filtered off and the filtrate was purified by chromatography using an ethyl acetate/hexane gradient. Yield: 67 mg, (51%). 7.81 (d, Ar, 1H, J=2.1 Hz), 7.73 (dd, Ar 1H, 2.1 Hz, J=8.6 Hz), 7.22 (s, Ar, 1H), 7.07 (d, Ar, 1H, J=8.6 Hz), 6.96 (s, Ar, 1H), 4.00 (s, $OCH_3$, 3H), 3.93 (s, $OCH_3$, 3H), 2.27 (s, $CH_3$, 3H), 1.90 (m, cyclopropyl, 2H), 1.37 (m, cyclopropyl, 2H), Example 104

2-[1-(2-Benzyloxy-phenyl)-cyclopropyl]-4-(2-chloro-4-methoxy-5-methyl-phenyl)-5-methyl-thiazole The title molecule was synthesized by cyclopropanation of 2-benzyloxy phenylacetonitrile followed by conversion to the thioamide and hantzsch thiazole formation (vide supra). The product was purified by chromatography on silica using an ethyl acetate/hexane gradient. Yield: 1.62 g (45%). $[MH]^+$ 476.2.

Example 126

2-{1-[4-(2-Chloro-4-methoxy-5-methyl-phenyl)-5-methyl-thiazol-2-yl]-cyclopropyl}-phenol 2-[1-(2-Benzyloxy-phenyl)-cyclopropyl]-4-(2-chloro-4-methoxy-5-methyl-phenyl)-5-methyl-thiazole (0.95 g, 2 mmol) was dissolved in dry ethanol (100 mL) 30% palladium on carbon (0.39 g, 1.1 mmol) and 1,4-cyclohexadiene (20 mL, 210 mmol) was added. The reaction mixture was stirred for 2 d at room temperature. The mixture was filtered through Celite concentrated, and purified by chromatography on silica using an ethyl acetate/hexane gradient, the title compound was obtained as a white powder. Yield: 0.41 g (53%). [MH]$^+$ =386.2, 388.2.

Example 117

(2-{1-Chloro-4-methoxy-5-methyl-phenyl)-5-methyl-thiazol-2-yl]-cyclopropyl}-phenoxy)-acetic acid methyl ester 2-{1-[4-(2-Chloro-4-methoxy-5-methyl-phenyl)-5-methyl-thiazol-2-yl]-cyclopropyl}-phenol (15 mg, 0.04 mmol) was dissolved in tetrahydrofuran (THF) (1 ml), treated with 1.1 mg NaH (0.044 mmol) at room temperature and stirred for 30 min. Methyl bromoacetate (7 mg, 0.044 mmol) was then added to the reaction vessel. The reaction mixtures was stirred overnight. The reaction mixture was quenched with 0.5 ml water and the THF removed in vacuo The residue was partitioned between ethyl acetate and water and the organic solution was separated and concentrated in vacuo then dissolved in methanol/dimethylsulfoxide 1:1 and purified via reversed phase HPLC chromatography (vide supra). Yield: 10.2 mg (56%). [MH]$^+$ 458.2, 460.0.

Example 115

(2-{1-[4-(2-Chloro-4-methoxy-5-methyl-phenyl)-5-methyl-thiazol-2-yl]-cyclopropyl}-phenoxy)-acetonitrile 2-{1-[4-(2-Chloro-4-methoxy-5-methyl-phenyl)-5-methyl-thiazol-2-yl]-cyclopropyl}-phenol (Example 126) (15 mg, 0.04 mmol) was dissolved in tetrahydrofuran (THF) (1 ml), treated with 1.1 mg NaH (0.044 mmol) at room temperature and stirred for 30 min. Bromoacetonitrile (5.5 mg, 0.044 mmol) was then added to the reaction vessel. The reaction mixtures was stirred overnight. The reaction mixture was quenched with 0.5 ml water and the THF removed in vacuo The residue was partitioned between ethyl acetate and water and the organic solution was separated and concentrated in vacuo then dissolved in methanol/dimethylsulfoxide (DMSO) 1:1 and purified via reversed phase HPLC chromatography (vide supra). Yield 11.5 mg (68%). [MH]$^+$ 425.0, 427.0.

Example 250

1-(2,4-Dichloro-phenyl)-cyclopropanecarboxylic acid amide 1-(2,4-Dichloro-phenyl)-cyclopropanecarbonitrile (2.1 g, 10 mmol) was dissolved in DMSO (10 ml) and the solution cooled to 0° C. using an ice bath. Potassium carbonate (0.2 g, 1.5 mmol) was then added, followed by commercial 30% aqueous hydrogen peroxide (2 mL). The reaction was then allowed to warm to room temperature with stirring over 1 h. Water (20 mL) was added and the 1-(2,4-dichloro-phenyl)-cyclopropanecarboxylic acid amide collected as a white solid. Yield: 2.1 g (90%).

4-(2-Chloro-4-methoxy-5-methyl-phenyl)-2-[1-(2,4-dichloro-phenyl) cyclopropyl]-5-methyl-oxazole 1-(2,4-Dichloro-phenyl)-cyclopropanecarboxylic acid amide (46 mg, 0.2 mmol) and 2-Bromo-1-(2-chloro-4-methoxy-5-methly-phenyl)-propan-1-one (58 mg, 0.2 mmol) were combined in DMF (1 mL) at 0.2 M and the mixture heated to 80° C. overnight. The reaction was then cooled to room temperature. The desired product was purified by reversed phase HPLC/MS using an acetonitrile/water gradient and C$_{18}$ stationary phase. Yield: 1 mg (2%) [MH]$^+$ 424.2, 422.2, 426.0 (small).

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12-18 and the coding region was amplified by PCR from start to stop codons. The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately 1×10$^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM MgCl$_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from 10$^{-10}$31 10$^{-5}$ M), 100 μl of $^{125}$I–ovine–CRF ($^{125}$I–o–CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40-60 mg protein). Reactions are initiated by the addition of 1 mM ATP/$^{32}$P] ATP (approximately 2-4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

The compounds of this invention may also be used as reagents or standards in the biochemical study of neurological function, dysfunction, and disease.

As those skilled in the art will appreciate, numerous changes and modifications can be made to the preferred embodiments of the invention without departing from the spirit of the invention. It is intended that all such variations fall within the scope of the invention. Throughout this specification, various groupings are employed to conveniently describe constituent variables of compounds and groups of various related moieties. It is specifically intended that each occurrence of such groups throughout this specification include every possible subcombination of the members of the groups, including the individual members thereof.

It is intended that each of the patents, applications, and printed publications mentioned in this patent document be hereby incorporated by reference in its entirety.

What is claimed is:

1. A compound of Formula (Ia):

(Ia)

or a pharmaceutically acceptable salt form thereof, wherein:

$R^1$ is Me, $R^{16a}$ is benzyl, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is m-CN-benzyl, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is —C≡CH, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is —C≡CH, $R^{16b}$ is H, $R^{16c}$ is H, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is —C≡CH, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is F and $R^{17e}$ is H; or $R^1$ is Me, $R^{16a}$ is —C≡CH, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is H, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is F, $R^{17b}$ is H, $R^{17c}$ is $CF_3$, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is Br and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Cl, $R^{16b}$ is Cl, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is Cl, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is H, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is F, $R^{17b}$ is H, $R^{17c}$ is F, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is Me, $R^{17d}$ is Cl and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is Me, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is $NMe_2$, $R^{17d}$ is Br and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is $OCHF_2$, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is OEt, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is H, $R^{17b}$ is H, $R^{17c}$ is SMe, $R^{17d}$ is H and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is OMe, $R^{17b}$ is H, $R^{17c}$ is OMe, $R^{17d}$ is Br and $R^{17e}$ is H; or $R^1$ is Me, $R^{16a}$ is Cl, $R^{16b}$ is H, $R^{16c}$ is Cl, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is F, $R^{17b}$ is H, $R^{17c}$ is $CF_3$, $R^{17d}$ is H and $R^{17e}$ is H; or $R^1$ is Me, $R^{16a}$ is Cl, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is F, $R^{17a}$ is Cl, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is Cl, $R^{17b}$ is H, $R^{17c}$ is H, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is F, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is Cl, $R^{17b}$ is H, $R^{17c}$ is OMe, $R^{17d}$ is Me and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is H, $R^{17b}$ is H, $R^{17c}$ is $CF_3$, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is H, $R^{17b}$ is H, $R^{17c}$ is Me, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is Cl, $R^{17a}$ is H, $R^{17b}$ is H, $R^{17c}$ is OMe, $R^{17d}$ is H and $R^{17e}$ is H; or $R^1$ is Me, $R^{16a}$ is Cl, $R^{16b}$ is H, $R^{16c}$ is H, $R^{16d}$ is H, $R^{16e}$ is F, $R^{17a}$ is OMe, $R^{17b}$ is H, $R^{17c}$ is OMe, $R^{17d}$ is H and $R^{17e}$ is H; or $R^1$ is Me, $R^{16a}$ is CN, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is CN, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is CN, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is CN, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is 5-tetrazolyl, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is $CO_2Me$, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is F, $R^{16b}$ is F, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is F, $R^{16b}$ is F, $R^{16c}$ is H, $R^{16d}$ is H, $R^{16e}$ is H, $R^{17a}$ is H, $R^{17b}$ is H, $R^{17c}$ is OMe, H is $R^{17d}$ and $R^{17e}$ is H; or $R^1$ is Me, $R^{16a}$ is F, $R^{16b}$ is H, $R^{16c}$ is H, $R^{16d}$ is F, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is F, $R^{16b}$ is H, $R^{16c}$ is H, $R^{16d}$ is F, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is F, $R^{16b}$ is H, $R^{16c}$ is H, $R^{16d}$ is F, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is F, $R^{16b}$ is H, $R^{16c}$ is H, $R^{16d}$ is F, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is F, $R^{16b}$ is H, $R^{16c}$ is H, $R^{16d}$ is H, $R^{16e}$ is Cl, $R^{17a}$ is H, $R^{17b}$ is H, $R^{17c}$ is Cl, $R^{17d}$ is H and $R^{17e}$ is H; or $R^1$ is Me, $R^{16a}$ is F, $R^{16b}$ is H, $R^{16c}$ is H, $R^{16d}$ is H, $R^{16e}$ is Cl, $R^{17a}$ is H, $R^{17b}$ is H, $R^{17c}$ is OMe, $R^{17d}$ is H and $R^{17e}$ is H; or $R^1$ is Me, $R^{16a}$ is F, $R^{16b}$ is H, $R^{16c}$ is H, $R^{16d}$ is H, $R^{16e}$ is F, $R^{17a}$ is Cl, $R^{17b}$ is H, $R^{17c}$ is Cl, $R^{17d}$ is H and $R^{17e}$ is H; or $R^1$ is Me, $R^{16a}$ is F, $R^{16b}$ is H, $R^{16c}$ is H, $R^{16d}$ is H, $R^{16e}$ is F, $R^{17a}$ is H, $R^{17b}$ is H, $R^{17c}$ is OMe, $R^{17d}$ is H and $R^{17e}$ is H; or $R^1$ is Me, $R^{16a}$ is F, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is F and $R^{17e}$ is H; or $R^1$ is Me, $R^{16a}$ is H, $R^{16b}$ is $CF_3$, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is H, $R^{16b}$ is Cl, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is H, $R^{16b}$ is Cl, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is H, $R^{16b}$ is Cl, $R^{16c}$ is H, $R^{16d}$ is H, $R_{16e}$ is H, $R^{17a}$ is H, $R^{17b}$ is H, $R^{17c}$ is Me, $R^{17d}$ is H and $R^{17e}$ is H; or $R^1$ is Me, $R^{16a}$ is H, $R^{16b}$ is F, $R^{16c}$ is H, $R^{16d}$ is F, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is H, $R^{16b}$ is F, $R^{16c}$ is H, $R^{16d}$ is H, $R^{16e}$ is H, $R^{17a}$ as H, $R^{17b}$ is H, $R^{17c}$ is OMe, $R^{17d}$ is H and $R^{17e}$ is H; or $R^1$ is Me, $R^{16a}$ is H, $R^{16b}$ is H, $R^{16c}$ is Cl, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is H, $R^{16b}$ is H, $R^{16c}$ is Cl, $R^{16d}$ H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is H, $R^{16b}$ is H, $R^{16c}$ is Cl, $R^{16d}$ is H, $R^{16e}$ H, $R^{17a}$ is H, $R^{17b}$ is H, $R^{17c}$ is OEt, $R^{17d}$ is H and $R^{17e}$ is H; or $R^1$ is Me, $R^{16a}$ is H, $R^{16b}$ is H, $R^{16c}$ is F, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is H, $R^{16b}$ is H, $R^{16c}$ is F, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is H, $R^{16b}$ is H, $R^{16c}$ is F, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is H, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is F, R$^{17b}$ is H, R$^{17c}$ is H, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is H, R$^{17b}$ is H, R$^{17c}$ is Et, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is H, R$^{16b}$ is H, R$^{16c}$ is Me, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is OMe, R$^{16d}$ is H, H$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is H, R$^{16c}$ is OMe, R$^{16d}$ is H, R$^{16e}$ is H, R$^{17a}$ is H, R$^{17b}$ is H, R$^{17c}$ is Me, R$^{17d}$ is H and R$^{17e}$ is H; or R$^1$ is Me, R$^{16a}$ is H, R$^{16b}$ is H, R$^{16c}$ is OMe, R$^{16d}$ is H, R$^{16e}$ is H, R$^{17a}$ is H, R$^{17b}$ is H, R$^{17c}$ is SMe, R$^{17d}$ is H and R$^{17e}$ is H; or R$^1$ is Me, R$^{16a}$ is H, R$^{16b}$ is Me, R$^{16c}$ is F, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ is OMe, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is H, R$^{16b}$ is OMe, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is H, R$^{16b}$ is OMe, R$^{16c}$ is OMe, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is I, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is I, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is I, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is Me, R$^{16b}$ is H, R$^{16c}$ is F, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is Me, R$^{16b}$ is H, R$^{16c}$ is H, R$^{16d}$ is F, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is Me, R$^{16b}$ is H, R$^{16c}$ is H, R$^{16d}$ is H, R$^{16e}$ is F, R$^{17a}$ is Me, R$^{17b}$ is H, R$^{17c}$ is Me, R$^{17d}$ is H and R$^{17e}$ is H ; or R$^1$ is Me, R$^{16a}$ is Me, R$^{16b}$ is H, R$^{16c}$ is H, R$_{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OBn, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is OBn, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is OC$_2$H$_4$OMe, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OCF$_3$, R$^{16b}$ is H, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is OCF$_3$, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is H and R$^{17e}$ is H; or R$^1$ is Me, R$^{16a}$ is OCF$_3$, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is OCF$_3$, R$^{16b}$ is H, R$^{16c}$ is H, R$^{16d}$ is H, R$^{16e}$ is H, R$^{17a}$ is H, R$^{17b}$ is H, R$^{17c}$ is Cl, R$^{17d}$ is H and R$^{17e}$ is H; or R$^1$ is Me, R$^{16a}$ is OCF$_3$, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is OCF$_3$, R$^{16b}$ is H, R$^{16c}$ is H, R$^{16d}$ is H, R$^{16e}$ is H, R$^{17a}$ is Me, R$^{17b}$ is H, R$^{17c}$ is Me, R$^{17d}$ is H and R$^{17e}$ is H; or R$^1$ is Me, R$^{16a}$ is OCH$_2$C≡CH, R$^{16b}$ is H, R$_{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OCH$_2$CHCH$_2$, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OCH$_2$CN, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is OCH$_2$CN, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OCH$_2$CO$_2$Me, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or R$^1$ is Me, R$^{16a}$ is OCH(Me)COMe, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OCH(Me)CO$_2$Et, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OCH(Me)CO$_2$Me, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OEt, R$^{16b}$ is H, R$^{16c}$ is H, R$^{16d}$ is H, R$^{16e}$ is H, R$^{17a}$ is Cl, R$^{17b}$ is H, R$^{17c}$ is Cl, R$^{17d}$ is H and R$^{17e}$ is H; or R$^1$ is Me, R$^{16a}$ is OEt, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is H and R$^{17e}$ is H; or R$^1$ is Me, R$^{16a}$ is OEt, R$^{16b}$ is H, R$^{16c}$ is H, R$^{16d}$ is H, R$^{16e}$ is H, R$^{17a}$ is H, R$^{17b}$ is H, R$^{17c}$ is OMe, R$^{17d}$ is H and R$^{17e}$ is H; or R$^1$ is Me, R$^{16a}$ is OEt, R$^{16b}$ is H, R$^{16c}$ is H, R$^{16d}$ is H, R$^{16e}$ is H, R$^{17a}$ is H, R$^{17b}$ is H, R$^{17c}$ is Cl, R$^{17d}$ is H and R$^{17e}$ is H; or R$^1$ is Me, R$^{16a}$ is OEt, R$^{16b}$ is H, R$^{16c}$ is H, R$^{16d}$ is H, R$^{16e}$ is H, R$^{17a}$ is OMe, R$^{17b}$ is H, R$^{17c}$ is OMe, R$^{17d}$ is H and R$^{17e}$ is H; or R$^1$ is Me, R$^{16a}$ is OH, R$^{16b}$ is H, R$^{16c}$ is H, R$^{16d}$ is H, R$^{16e}$ is H, R$^{17a}$ is Cl, R$^{17b}$ is H, R$^{17c}$ is OMe, R$^{17d}$ is Me and R$^{17e}$ is H; or $R^1$ is Me, $R^{16a}$ is OMe, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is Cl, $R^{17b}$ is H, $R^{17c}$ is Cl $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is Cl, $R^{17b}$ is H, $R_{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Br, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is $CH_2COMe$, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is CH(OH)Me, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is $CH(OH)CMe_3$, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is CN, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is CN, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is COMe, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is $OMe_2$, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OMe, $R^{16b}$ is H, $R^{16c}$ is H, $R^{16d}$ is F, $R^{16e}$ is F, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is F, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is $CF_3$, $R^{17b}$ is H, $R^{17c}$ is $CF_3$, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is $CH_2OH$, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is H, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is CN, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is $CO_2Me$, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is F, $R^{17b}$ is H, $R^{17c}$ is $CF_3$, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is $CF_3$, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is Me, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is F and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is I, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is Me, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OMe, $R^{16b}$ is H, $R^{16c}$ is H, $R^{16d}$ is Me, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OMe, $R^{16b}$ is OMe, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is OPh, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is Ph, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is Ph, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is Me, $R^{16a}$ is $SCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Me, $R^{16a}$ is $SCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is Me, $R^{16a}$ is $SCF_3$, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is Me, $R^{16a}$ is $SCF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Me, $R^{16a}$ is SMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Br, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $CH_2OH$, $R^{16a}$ is $CF_3$, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is CHO, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is (CH(OH)Me, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CN, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is COMe, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is I, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $SCF_3$, $R^{16a}$ is $CF_3$, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $CH_2OH$, $R^{16a}$ is Cl, $R^{16b}$ is H, $R^{16c}$ is Cl, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CHO, $R^{16a}$ is H, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is (C=O)cPr, $R^{16a}$ is H, $R^{16b}$ is H, $R^{16c}$ is F, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CHO, $R^{16a}$ is $OCF_3$, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is CH(OH)Me, $R^{16a}$ is $OCF_3$, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is CH(OH)Me, $R^{16a}$ is OEt, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is I, $R^{16a}$ is OEt, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is Br, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is Br, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is $CF_3$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $CH_2CHO$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is Cl, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is H, $R^{17b}$ is H, $R^{17c}$ is OMe, $R^{17d}$ is H and $R^{17e}$ is H; or $R^1$ is $CH_2OH$, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $CHF_2$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is CHO, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is $CF_3$, $R^{17b}$ is H, $R^{17c}$ is $CF_3$, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is CH(OH)Me, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is COMe, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is COMe, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me ad $R^{17e}$ is H; or $R^1$ is $CO_2Me$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is $CF_3$, $R^{17b}$ is H, $R^{17c}$ is $CF_3$, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is OMe, $R^{17d}$ is Me and $R^{17e}$ is H; or $R^1$ is I, $R^{16a}$ is OMe, $R^{16b}$ is H, $R^{16c}$ is H, $R^{16d}$ is H, $R^{16e}$ is H $R^{17a}$ is Me, $R^{17b}$ is H, $R^{17c}$ is Me, $R^{17d}$ is H and $R^{17e}$ is H; or $R^1$ is I, $R^{16a}$ is OMe, $R^{16b}$ is H, $R^{16c}$ is H, $R^{16d}$ is H, $R^{16e}$ is H, $R^{17a}$ is OMe, $R^{17b}$ is H, $R^{17c}$ is OMe, $R^{17d}$ is H and $R^{17e}$ is H; or $R^1$ is $NH_2$, $R^{16a}$ is OMe, $R^{16b}$ is H, $R^{16c}$ is H, $R^{16d}$ is H, $R^{16e}$ is $R^{17a}$ is Cl, $R^{17b}$ is H, $R^{17c}$ is Cl, $R^{17d}$ is H and $R^{17e}$ is H; or $R^1$ is $NO_2$, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is SMe, $R^{16a}$ is OMe, $R^{16b}$ is H, $R^{16c}$ is H, $R^{16d}$ is H, $R^{16e}$ is H, $R^{17a}$ is Cl, $R^{17b}$ is H, $R^{17c}$ is Cl, $R^{17d}$ is H and $R^{17e}$ is H; or $R^1$ is SMe, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is H; or $R^1$ is Me, $R^{16a}$ is $CF_3$, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is Me; or $R^1$ is Me, $R^{16a}$ is Cl, $R^{16b}$ is H, $R^{16c}$ is F, $R^{16d}$ is H, $R^{16e}$ is H, $R^{17a}$ is Me, $R^{17b}$ is H, $R^{17c}$ is Me, $R^{17d}$ is H and $R^{17e}$ is Me; or $R^1$ is Me, $R^{16a}$ is F, $R^{16b}$ is H, $R^{16c}$ is H, $R^{16d}$ is H, $R^{16e}$ is Cl, $R^{17a}$ is Me, $R^{17b}$ is H, $R^{17c}$ is Me, $R^{17d}$ is H and $R^{17e}$ is Me; or $R^1$ is Me, $R^{16a}$ is H, $R^{16b}$ is H, $R^{16c}$ is H, $R^{16d}$ is H, $R^{16e}$ is H, $R^{17a}$ is F, $R^{17b}$ is H, $R^{17c}$ is H, $R^{17d}$ is H and $R^{17e}$ is $CF_3$; or $R^1$ is Me, $R^{16a}$ is OMe, $R^{16b}$ is H, $R^{16c}$ is H, $R^{16d}$ is H, $R^{16e}$ is H, $R^{17a}$ is F, $R^{17b}$ is H, $R^{17c}$ is H, $R^{17d}$ is H and $R^{17e}$ is $CF_3$; or $R^1$ is Me, $R^{16a}$ is OMe, $R^{16b}$ is H, $R^{16c}$ is H, $R^{16d}$ is H, $R^{16e}$ is H, $R^{17a}$ is Me, $R^{17b}$ is H, $R^{17c}$ is Me, $R^{17d}$ is H and $R^{17e}$ is Me.

2. A compound of Formula (Ib):

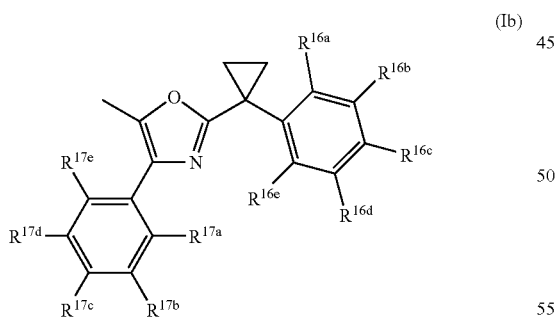

(Ib)

or a pharmaceutically acceptable salt form thereof, wherein:

$R^{16a}$ is Cl, $R^{16b}$ is H $R^{16c}$ is H, $R^{16d}$ is H $R^{16e}$ is H $R^{17a}$ is H, $R^{17b}$ is $CF_3$, $R^{17c}$ is F, $R^{17d}$ is H and $R^{17e}$ is H; or $R^{16a}$ is Cl, $R^{16b}$ is H $R^{16c}$ is Cl $R^{16d}$ is H $R^{16e}$ is H, $R^{17a}$ is Cl, $R^{17b}$ is H, $R^{17c}$ is Cl, $R^{17d}$ is H and $R^{17e}$ is H; or $R^{16a}$ is Cl, $R^{16b}$ is H $R^{16c}$ is Cl $R^{16d}$ is H $R^{16e}$ is H, $R^{17a}$ is $CF_3$, $R^{17b}$ is H, $R^{17c}$ is H, $R^{17d}$ is H and $R^{17e}$ is F; or $R^{16a}$ is OMe, $R^{16b}$ is H $R^{16c}$ is H $R^{16d}$ is H $R^{16e}$ is H, $R^{17a}$ is Cl, $R^{17b}$ is H, $R^{17c}$ is H, $R^{17d}$ is H and $R^{17e}$ is H; or $R^{16a}$ is Cl, $R^{16b}$ is H $R^{16c}$ is Cl, $R^{16d}$ is H $R^{16e}$ is H, $R^{17a}$ is Cl, $R^{17b}$ is H, $R^{17c}$ is OMe, $R^{17d}$ is Me and $R^{17e}$ is H.

3. A pharmaceutical composition comprising a pharmaceutically acceptable carrier and a compound of Formula (I):

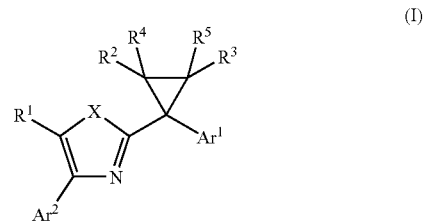

(I)

or a pharmaceutically acceptable salt form thereof, wherein:

X is O or S;

$R^1$ is $C_1$-$C_6$ alkyl;

each $R^2$ and $R^4$ is, independently, H, halogen, $C_1$-$C_6$ alkyl, $C_1$-$C_6$ haloalkyl, —CN, —$NO_2$, $C_3$-$C_6$ cycloalkyl, —$NR^8R^9$, —$NR^8COR^9$, —$COR^8$, —$CO_2R^8$, —$OR^8$, —$SR^8$, —$S(O)_nR^8$, —$CH(OH)R^8$, or —$CH_2COR^8$;

each $R^3$ and $R^5$ is, independently, H, halogen, $C_1$-$C_6$ alkyl, $C_1$-$C_6$ haloalkyl, —CN, —$NO_2$, $C_3$-$C_6$ cycloalkyl, —$NR^{10}R^{11}$, —$NR^{10}COR^{11}$, —$COR^{10}$, —$CO_2R^{10}$, —$OR^{10}$, —$SR^{10}$, —$S(O)_nR^{10}$, —$CH(OH)R^{10}$, or —$CH_2COR^{10}$;

each $R^8$ and $R^9$ is, independently, at each occurrence, H, $C_1$-$C_6$ alkyl, $C_1$-$C_6$ haloalkyl, or $C_3$-$C_6$ cycloalkyl, wherein each $R^8$ and $R^9$ is optionally substituted with one or more halogen, hydroxyl, or —CN;

each $R^{10}$ and $R^{11}$ is, independently, at each occurrence, H, $C_1$-$C_6$ alkyl, $C_1$-$C_6$ haloalkyl, or $C_3$-$C_6$ cycloalkyl, wherein each $R^{10}$ and $R^{11}$ is optionally substituted with one or more halogen, hydroxyl, or —CN;

each $R^{12}$ and $R^{13}$ is, independently, at each occurrence, H, —$NH_2$, $C_1$-$C_6$ alkyl, $C_1$-$C_6$ haloalkyl, $C_3$-$C_6$ cycloalkyl, aryl, heteroaryl, or heterocyclyl, wherein each $R^{12}$ and $R^{13}$ is optionally substituted with one or more halogen, hydroxyl, or —CN;

each $R^{14}$ and $R^{15}$ is, independently, at each occurrence, H, —$NH_2$, $C_1$-$C_6$ alkyl, $C_1$-$C_6$ haloalkyl, $C_3$-$C_6$ cycloalkyl, aryl, heteroaryl, or heterocyclyl, wherein each $R^{14}$ and $R^{15}$ is optionally substituted with one or more halogen, hydroxyl, or —CN;

$R^{16}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, aryl-$C_1$-$C_6$ alkyl, —CN, —$CH_2CN$, —$CH_2OR^{12}$, $CH_2NR^{12}R^{13}$, —$CH_2OH$, —$NO_2$, $C_3$-$C_6$ cycloalkyl, —$NR^{12}R^{13}$, —$NR^{12}COR^{13}$, —$NHSO_2R$, —$COR^{12}$, —$CO_2R^{12}$, —$OR^{12}$, —$OC_2H_4OR^{12}$, —$SR^{12}$, —$S(O)_nR^{12}$, —$S(O)_nNR^{12}R^{13}$, —$CH(OH)R^{12}$, —$CH_2COR^{12}$, —$OC(O)R^{12}$, —$OCHR^{12}CO_2R^{13}$, —$OCHR^{12}COR^{13}$, —$NR^{12}CONR^{12}R^{13}$, —$NR^{12}CO_2R^{13}$, —$CONR^{12}R^{13}$, or —$CH(OH)C(R^{12})_3$;

$R^{17}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{14}$, $CH_2NR^{14}R^{15}$, —$CH_2OH$, —$NO_2$, $C_3$-$C_6$ cycloalkyl, —$NR^{14}R^{15}$, —$NR^{14}COR^{15}$, —$NHSO_2R$, —$COR^{14}$, —$CO_2R^{14}$, —$OR^{14}$, —$OC_2H_4OR^{14}$, —$SR^{14}$, —$S(O)_nR^{14}$, —$S(O)_nNR^{14}R^{15}$, —$CH(OH)R^{14}$, —$CH_2COR^{14}$, —OC(O)R$^{14}$, —OCHR$^{14}$CO$_2$R$^{15}$, —OCHR$^{14}$COR$^{15}$, —NR$^{14}$CONR$^{14}$R$^{15}$, —NR$^{14}$CO$_2$R$^{15}$, —CONR$^{14}$R$^{15}$, or —CH(OH)C(R$^{14}$)$_3$;

each R$^{18}$ and R$^{19}$ is, independently, at each occurrence, H, C$_1$-C$_6$ alkyl, C$_1$-C$_6$ haloalkyl, or C$_3$-C$_6$ cycloalkyl, wherein each R$^{18}$ and R$^{19}$ is optionally substituted with one or more halogen, hydroxyl, or —CN;

R$^{20}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{21}$, CH$_2$NR$^{21}$R$^{22}$, —CH$_2$OH, —NO$_2$, C$_3$-C$_6$ cycloalkyl, —NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^{21}$ and R$^{22}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each R$^{21}$ and R$^{22}$ is optionally substituted with one or more halogen, hydroxyl, or —CN;

R$^{23}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$^{20}$R$^{24}$, CH$_2$NR$^{24}$R$^{25}$, —CH$_2$OH, —NO$_2$, C$_3$C$_6$ cycloalkyl, —NR$^{24}$R$^{25}$, —NR$^{24}$COR$^{25}$, —NHSO$_2$R, —COR$^{24}$, —CO$_2$R$^{24}$, —OR$^{24}$, —OC$_2$H$_4$OR$^{24}$, —SR$^{24}$, —S(O)$_n$R$^{24}$, —S(O)$_n$NR$^{24}$R$^{25}$, —CH(OH)R$^{24}$, —CH$_2$COR$^{24}$, —OC(O)R$^{24}$, —OCHR$^{24}$CO$_2$R$^{25}$, —OCHR$^{24}$COR$^{25}$, —NR$^{24}$CONR$^{24}$R$^{25}$, —NR$^{24}$CO$_2$R$^{25}$, —CONR$^{24}$R$^{25}$, or —CH(OH)C(R$^{24}$)$_3$;

each R$^{24}$ and R$^{25}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl or heterocyclyl, wherein each R$^{24}$ and R$^{25}$ is optionally substituted with one or more halogen, hydroxyl, or —CN;

Ar$^1$ is phenyl optionally substituted with 1 to 5 R$^{16}$ groups; and wherein two of said R$^{16}$ groups, each attached to adjacent carbon atoms of said Ar$^1$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{20}$ groups;

Ar$^2$ is phenyl optionally substituted with 1 to 5 R$^{17}$ groups; and wherein two of said R$^{17}$ groups, each attached to adjacent carbon atoms of said Ar$^2$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{23}$ groups;

n is 0,1, or 2;

aryl is phenyl or naphthyl, wherein said aryl is optionally substituted with 1 to 10 substituents independently selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, wherein said heteroaryl is optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$ or —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$; and heterocyclyl is saturated or partially saturated heteroaryl, optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$.

4. The pharmaceutical composition of claim 3 wherein R$^1$ is methyl.

5. A pharmaceutical composition comprising a pharmaceutically acceptable carrier and a compound of Formula (I):

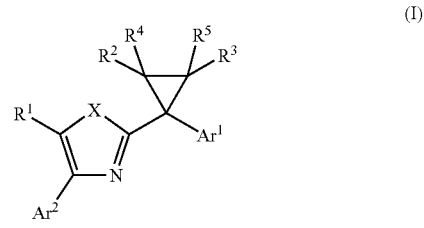

(I)

or a pharmaceutically acceptable salt form thereof, wherein:

X is O;

R$^1$ is H, halogen, C$_1$-C$_6$ alkyl, C$_1$-C$_6$ haloalkyl, —CN, —NO$_2$, C$_3$-C$_6$ cycloalkyl, —NR$^6$R$^7$, —NR$^6$COR$^7$, —COR$^6$, —CO$_2$R$^6$, —OR$^6$, —SR$^6$ or —S(O)$_n$R$^6$, —CH(OH)R$^6$, or —CH$_2$COR$^6$;

each R$^2$ and R$^4$ is, independently, H, halogen, C$_1$-C$_6$ alkyl, C$_1$-C$_6$ haloalkyl, —CN, —NO$_2$C$_3$-C$_6$ cycloalkyl, —NR$^8$R$^9$, —NR$^8$COR$^9$, —COR$^8$, —CO$_2$R$^8$, —OR$^8$, —SR$^8$. —S(O)$_n$R$^8$, —CH(OH)R$^8$, or —CH$_2$COR$^8$;

each R$^3$ and R$^5$ is, independently, H, halogen, C$_1$-C$_6$alkyl, C$_1$-C$_6$ haloalkyl, —CN, —NO$_2$, C$_3$-C$_6$ cycloalkyl, —NR$^{10}$R$^{11}$, —NR$^{10}$COR$^{11}$, —COR$^{10}$, —CO$_2$R$^{10}$, —OR$^{10}$, —SR$^{10}$; —S(O)$_n$R$^{10}$, —CH(OH)R$^{10}$, or —CH$_2$COR$^{10}$;

each R$^6$ and R$^7$ is, independently, at each occurrence, H, C$_1$-C$_6$ alkyl, C$_1$-C$_6$ haloalkyl, or C$_3$-C$_6$ cycloalkyl, wherein each of said R$^6$ and R$^7$ is optionally substituted with one or more halogen, hydroxyl, or —CN:

each R$^8$ and R$^9$ is, independently, at each occurrence, H, C$_1$-C$_6$ alkyl, C$_1$-C$_6$ haloalkyl, or C$_3$-C$_6$ cycloalkyl, wherein each R$^8$ and R$^9$ is optionally substituted with one or more halogen, hydroxyl, or —CN:

each R$^{10}$ and R$^{11}$ is, independently, at each occurrence, H, C$_1$-C$_6$ alkyl, C$_1$-C$_6$ haloalkyl, or C$_3$-C$_6$ cycloalkyl, wherein each R$^{10}$ and R$^{11}$ is optionally substituted with one or more halogen, hydroxyl, or —CN:

each R$^{12}$ and R$^{13}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each $R^{12}$ and $R^{13}$ is optionally substituted with one or more halogen, hydroxyl, or —CN:

each $R^{14}$ and $R^{15}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each $R^{14}$ and $R^{15}$ is optionally substituted with one or more halogen, hydroxyl, or —CN;

Ar$^1$ is phenyl, benzyl, pyridyl, or thienyl, wherein said Ar$^1$ is optionally substituted with 1 to 5 $R^{16}$ groups;

Ar$^2$ is phenyl, benzyl, or pyridyl, wherein Ar$^2$ is optionally substituted with 1 to 5 $R^{17}$ groups;

$R^{16}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, —CN, —COR$^{12}$, —CO$_2$R$^{12}$, —OR$^{12}$, —OC$_2$H$_4$OR$^{12}$, —SR$^{12}$, —CH(OH)R$^{12}$, —CH$_2$COR$^{12}$, or —CONR$^{12}$R$^{13}$;

$R^{17}$ is, at each occurrence, H, halogen, C$_1$-C$_6$ alkyl, C$_1$-C$_6$ haloalkyl, —CN, —CH$_2$OH, —NR$^{14}$R$^{15}$, —CO$_2$R$^{14}$, —OR$^{14}$, or —SR$^{14}$;

each $R^{18}$ and $R^{19}$ is, independently, at each occurrence, H, C$_1$-C$_6$ alkyl, C$_1$-C$_6$ haloalkyl, or C$_3$-C$_6$ cycloalkyl, wherein each $R^{18}$ and $R^{19}$ is optionally substituted with one or more halogen, hydroxyl, or —CN;

n is 0, 1, or 2;

aryl is phenyl or naphthyl, wherein said aryl is optionally substituted with 1 to 10 substituents independently selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$ or —CH(OH)C(R$^{18}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, wherein said heteroaryl is optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$ or —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$; and heterocyclyl is saturated or partially saturated heteroaryl, optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$.

6. A pharmaceutical composition comprising a pharmaceutically acceptable carrier and a compound of Formula (Ic):

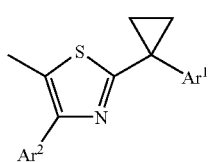

(Ic)

or a pharmaceutically acceptable salt form thereof, wherein:

Ar$^1$ is 3-methyl-thien-2-yl and Ar$^2$ is 2,4-dimethoxy-phenyl; or

Ar$^1$ is 2-methoxy-phenyl and Ar$^2$ is 2,6-dimethyl-pyrid-3-yl; or

Ar$^1$ is 3-methyl-pyrid-2-yl and Ar$^2$ is 3-bromo-4-methoxy-phenyl; or

Ar$^1$ is 3-methyl-pyrid-2-yl and Ar$^2$ is 2,4-dichloro-phenyl; or

Ar$^1$ is 3-methyl-pyrid-2-yl and Ar$^2$ is 4-trifluoromethyl-phenyl; or

Ar$^1$ is 3-chloro-5-trifluoromethyl-pyrid-2-yl and Ar$^2$ is 3-bromo-4-methoxy-phenyl; or Ar$^1$ is 3-chloro-5-trifluoromethyl-pyrid-2-yl and Ar$^2$ is 2,4-dichloro-phenyl; or Ar$^1$ is 3-methyl-pyrid-2-yl and Ar$^2$ is 4-methoxy-phenyl; or Ar$^1$ is 3-methyl-pyrid-2-yl and Ar$^2$ is 4-chloro-phenyl; or Ar$^1$ is 3-methyl-pyrid-2-yl and Ar$^2$ is 2,4-dichloro-phenyl; or Ar$^1$ is 2-methoxy-phenyl and Ar$^2$ is 6-methyl-pyrid-3-yl; or Ar$^1$ is 2-trifluoromethoxy-phenyl and Ar$^2$ is 6-methyl-pyrid-3-yl; or Ar$^1$ is 2,6-dichloro-phenyl and Ar$^2$ is 6-methoxy-pyrid-3-yl; or Ar$^1$ is 2,6-dichloro-phenyl and Ar$^2$ is 2,6-dimethyl-pyrid-3-yl; or Ar$^1$ is 2-trifluoromethyl-phenyl and Ar$^2$ is 2,6-dimethyl-pyrid-3-yl; or Ar$^1$ is 2-trifluoromethoxy-phenyl and Ar$^2$ is 2,6-dimethyl-pyrid-3-yl; or Ar$^1$ is 3-methoxy-pyrid-2-yl and Ar$^2$ is 2-chloro-4-methoxy-5-methyl-phenyl; or Ar$^1$ is 2-bromo-5-methoxy-phenyl and Ar$^2$ is 2,6-dimethyl-pyrid-3-yl.

7. A pharmaceutical composition comprising:
a pharmaceutically acceptable carrier;
an antioxidizing agent; and
a compound of Formula (I):

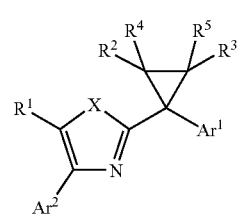

(I)

or a pharmaceutically acceptable salt form thereof, wherein:

X is O or S;

$R^1$ is H, halogen, C$_1$-C$_6$ alkyl, C$_1$-C$_6$ haloalkyl, —CN, —NO$_2$, C$_3$-C$_6$ cycloalkyl, —NR$^6$R$^7$, —NR$^6$COR$^7$, —COR$^6$, —CO$_2$R$^6$, —OR$^6$, —SR$^6$, —S(O)$_n$R$^6$, —CH(OH)R$^6$, or —CH$_2$COR$^6$;

each $R^2$ and $R^4$ is, independently, H, halogen, C$_1$-C$_6$ alkyl, C$_1$-C$_6$ haloalkyl, —CN, —NO$_2$, C$_3$-C$_6$ cycloalkyl, —NR$^8$R$^9$, NR$^8$COR$^9$, COR$^8$, CO$_2$R$^8$, —OR$^8$, —SR$^8$, —S(O)$_n$R$^8$, —CH(OH)R$^8$, or —CH$_2$COR$^8$;

each $R^3$ and $R^5$ is, independently, H, halogen, C$_1$-C$_6$ alkyl, C$_1$-C$_6$ haloalkyl, —CN, —NO$_2$, C$_3$-C$_6$ cycloalkyl, —NR$^{10}$R$^{11}$, —NR$^{10}$COR$^{11}$, —COR$^{10}$, —CO$_2$R$^{10}$, —OR$^{10}$, —SR$^{10}$, —S(O)$_n$R$^{10}$, —CH(OH)R$^{10}$, or —CH$_2$COR$^{10}$;

each R$^6$ and R$^7$ is, independently, at each occurrence, H, C$_1$-C$_6$ alkyl, C$_1$-C$_6$ haloalkyl, or C$_3$-C$_6$ cycloalkyl, wherein each of said R$^6$ and R$^7$ is optionally substituted with one or more halogen, hydroxyl, or —CN;

each R$^8$ and R$^9$ is, independently, at each occurrence, H, C$_1$-C$_6$ alkyl, C$_1$-C$_6$ haloalkyl, or C$_3$-C$_6$ cycloalkyl, wherein each R$^8$ and R$^9$ is optionally substituted with one or more halogen, hydroxyl, or —CN;

each R$^{10}$ and R$^{11}$ is, independently, at each occurrence, H, C$_1$-C$_6$ alkyl, C$_1$-C$_6$ haloalkyl, or C$_3$-C$_6$ cycloalkyl, wherein each R$^{10}$ and R$^{11}$ is optionally substituted with one or more halogen, hydroxyl, or —CN;

each R$^{12}$ and R$^{13}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each R$^{12}$ and R$^{13}$ is optionally substituted with one or more halogen, hydroxyl, or —CN;

each R$^{14}$ and R$^{15}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each R$^{14}$ and R$^{15}$ is optionally substituted with one or more halogen, hydroxyl, or —CN;

R$^{16}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, aryl-C$_1$-C$_6$ alkyl, —CN, —CH$_2$CN, —CH$_2$OR$^{12}$, CH$_2$NR$^{12}$R$^{13}$, —CH$_2$OH, —NO$_2$, C$_3$-C$_6$ cycloalkyl, —NR$^{12}$R$^{13}$, —NR$^{12}$COR$^{13}$, —NHSO$_2$R, —COR$^{12}$, —CO$_2$R$^{12}$, —OR$^{12}$, —OC$_2$H$_4$OR$^{12}$, —SR$^{12}$, —S(O)$_n$R$^{12}$, —S(O)$_n$NR$^{12}$R$^{13}$, —CH(OH)R$^{12}$, —CH$_2$COR$^{12}$, —OC(O)R$^{12}$, —OCHR$^{12}$CO$_2$R$^{13}$, —OCHR$^{12}$COR$^{13}$, —NR$^{12}$CONR$^{12}$R$^{13}$, —NR$^{12}$CO$_2$R$^{13}$, —CONR$^{12}$R$^{13}$, or —CH(OH)C(R$^{12}$)$_3$;

R$^{17}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{14}$, CH$_2$NR$^{14}$R$^{15}$, —CH$_2$OH, —NO$_2$, C$_3$-C$_6$ cycloalkyl, —NR$^{14}$R$^{15}$, —NR$^{14}$COR$^{15}$, —NHSO$_2$R, —COR$^{14}$, —CO$_2$R$^{14}$, —OR$^{14}$, —OC$_2$H$_4$OR$^{14}$, —SR$^{14}$, —S(O)$_n$R$^{14}$, —S(O)$_n$NR$^{14}$R$^{15}$, —CH(OH)R$^{14}$, —CH$_2$COR$^{14}$, —OC(O)R$^{14}$, —OCHR$^{14}$CO$_2$R$^{15}$, —OCHR$^{14}$COR$^{15}$, —NR$^{14}$CONR$^{14}$R$^{15}$, —NR$^{14}$CO$_2$R$^{15}$, —CONR$^{14}$R$^{15}$, or —CH(OH)C(R$^{14}$)$_3$;

each R$^{18}$ and R$^{19}$ is, independently, at each occurrence, H, C$_1$-C$_6$ alkyl, C$_1$-C$_6$ haloalkyl, or C$_3$-C$_6$ cycloalkyl, wherein each R$^{18}$ and R$^{19}$ is optionally substituted with one or more halogen, hydroxyl, or —CN;

R$^{20}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{21}$, CH$_2$NR$^{21}$R$^{22}$ —CH$_2$OH, —NO$_2$, C$_3$-C$_6$ cycloalkyl, —NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$ —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^{21}$ and R$^{22}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl, or heterocyclyl, wherein each R$^{21}$ and R$^{22}$ is optionally substituted with one or more halogen, hydroxyl, or —CN;

R$^{23}$ is, at each occurrence, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{24}$, CH$_2$NR$^{24}$R$^{25}$, —CH$_2$OH, —NO$_2$, C$_3$-C$_6$ cycloalkyl, —NR$^{24}$R$^{25}$, —NR$^{24}$COR$^{25}$, —NHSO$_2$R, —COR$^{24}$, —CO$_2$R$^{24}$, —OR$^{24}$, —OC$_2$H$_4$OR$^{24}$, —SR$^{24}$, —S(O)$_n$R$^{24}$, —S(O)$_n$NR$^{24}$R$^{25}$, —CH(OH)R$^{24}$, —CH$_2$COR$^{24}$, —OC(O)R$^{24}$, —OCHR$^{24}$CO$_2$R$^{25}$, —OCHR$^{24}$COR$^{25}$, —NR$^{24}$CONR$^{24}$R$^{25}$, —NR$^{24}$CO$_2$R$^{25}$, —CONR$^{24}$R$^{25}$, or —CH(OH)C(R$^{24}$)$_3$;

each R$^{24}$ and R$^{25}$ is, independently, at each occurrence, H, —NH$_2$, C$_1$-C$_6$ alkyl, C$_1$-C$_6$ haloalkyl, C$_3$-C$_6$ cycloalkyl, aryl, heteroaryl or heterocyclyl, wherein each R$^{24}$ and R$^{25}$ is optionally substituted with one or more halogen, hydroxyl, or —CN;

Ar$^1$ is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, indazolyl 3,4-dihydro-2H-benzo[1,4]oxazine, benzo[1,3]dioxole, or heterocyclyl, wherein Ar$^1$ is optionally substituted with 1 to 5 R$^{16}$ groups; and wherein two of said R$^{16}$ groups, each attached to adjacent carbon atoms of said Ar$^1$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{20}$ groups;

Ar$^2$ is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, indazolyl, 3,4-dihydro-2H-benzo[1,4]oxazine, benzo[1,3]dioxole, or heterocyclyl, wherein each Ar$^2$ is optionally substituted with 1 to 5 R$^{17}$ groups; and wherein two of said R$^{17}$ groups, each attached to adjacent carbon atoms of said Ar$^2$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{23}$ groups;

n is 0,1, or 2;

aryl is phenyl or naphthyl, wherein said aryl is optionally substituted with 1 to 10 substituents independently selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, or indazolyl, wherein said heteroaryl is optionally substituted with 1 to 10 substituents selected from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$ or —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$; and heterocyclyl is saturated or partially saturated heteroaryl, optionally substituted with 1 to 10 substituents selected from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$.

8. A method of treating a mammal having affective disorder, anxiety, or depression, said method comprising administering to said mammal a therapeutically effective amount of a compound of the Formula (I):

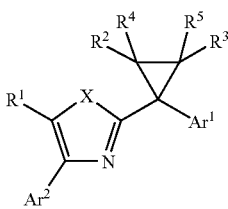

(I)

or a pharmaceutically acceptable salt form thereof, wherein:

X is O or S;

R$^1$ is H, halogen, $C_1$-$C_6$ alkyl, $C_1$-$C_6$ haloalkyl, —CN, —NO$_2$, $C_3$-$C_6$ cycloalkyl, —NR$^6$R$^7$, —NR$^6$COR$^7$, —COR$^6$, —CO$_2$R$^6$, —OR$^6$, —SR$^6$, —S(O)$_n$R$^6$, —CH(OH)R$^6$, or —CH$_2$COR$^6$;

each R$^2$ and R$^4$ is, independently, H, halogen, $C_1$-$C_6$ alkyl, $C_1$-$C_6$ haloalkyl, —CN, —NO$_2$, $C_3$-$C_6$ cycloalkyl, —NR$^8$R$^9$, —NR$^8$COR$^9$, —COR$^8$, —CO$_2$R$^8$, —OR$^8$, —SR$^8$, —S(O)$_n$R$^8$, —CH(OH)R$^8$, or —CH$_2$COR$^8$;

each R$^3$ and R$^5$ is, independently, H, halogen, $C_1$-$C_6$ alkyl, $C_1$-$C_6$ haloalkyl, —CN, —NO$_2$, $C_3$-$C_6$ cycloalkyl, —NR$^{10}$R$^{11}$, —NR$^{10}$COR$^{11}$, —COR$^{10}$, —CO$_2$R$_{10}$, —OR$^{10}$, —SR$^{10}$, —S(O)$_n$R$^{10}$, —CH(OH)R$^{10}$, or —CH$_2$COR$^{10}$;

each R$^6$ and R$^7$ is, independently, at each occurrence, H, $C_1$-$C_6$ alkyl, $C_1$-$C_6$ haloalkyl, or $C_3$-$C_6$ cycloalkyl, wherein each of said R$^6$ and R$^7$ is optionally substituted with one or more halogen, hydroxyl, or —CN;

each R$^8$ and R$^9$ is, independently, at each occurrence, H, $C_1$-$C_6$ alkyl, $C_1$-$C_6$ haloalkyl, or $C_3$-$C_6$ cycloalkyl, wherein each R$^8$ and R$^9$ is optionally substituted with one or more halogen, hydroxyl, or —CN;

each R$^{10}$ and R$^{11}$ is, independently, at each occurrence, H, $C_1$-$C_6$ alkyl, $C_1$-$C_6$ haloalkyl, or $C_3$-$C_6$ cycloalkyl, wherein each R$^{10}$ and R$^{11}$ is optionally substituted with one or more halogen, hydroxyl, or —CN;

each R$^{12}$ and R$^{13}$ is, independently, at each occurrence, H, —NH$_2$, $C_1$-$C_6$ alkyl, $C_1$-$C_6$ haloalkyl, $C_3$-$C_6$ cycloalkyl, aryl, heteroaryl, or heterocyclyl, wherein each R$^{12}$ and R$^{13}$ is optionally substituted with one or more halogen, hydroxyl, or —CN;

each R$^{14}$ and R$^{15}$ is, independently, at each occurrence, H, —NH$_2$, $C_1$-$C_6$ alkyl, $C_1$-$C_6$ haloalkyl, $C_3$-$C_6$ cycloalkyl, aryl, heteroaryl, or heterocyclyl, wherein each R$^{14}$ and R$^{15}$ is optionally substituted with one or more halogen, hydroxyl, or —CN;

R$^{16}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, aryl-$C_1$-$C_6$ alkyl, —CN, —CH$_2$CN, —CH$_2$OR$^{12}$, CH$_2$NR$^{12}$R$^{13}$, —CH$_2$OH, —NO$_2$, $C_3$-$C_6$ cycloalkyl, —NR$^{12}$R$^{13}$, —NR$^{12}$COR$^{13}$, —NHSO$_2$R, —COR$^{12}$, —CO$_2$R$^{12}$, —OR$^{12}$, —OC$_2$H$_4$OR$^{12}$, —SR$^{12}$, —S(O)$_n$R$^{12}$, —S(O)$_n$NR$^{12}$R$^{13}$, —CH(OH)R$^{12}$, —CH$_2$COR$^{12}$, —OC(O)R$^{12}$, —OCHR$^{12}$CO$_2$R$^{13}$, —OCHR$^{12}$COR$^{13}$, —NR$^{12}$CONR$^{12}$R$^{13}$, —NR$^{12}$CO$_2$R$^{13}$, —CONR$^{12}$R$^{13}$, or —CH(OH)C(R$^{12}$)$_3$;

R$^{17}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{14}$, CH$_2$NR$^{14}$R$^{15}$, —CH$_2$OH, —NO$_2$, $C_3$-$C_6$ cycloalkyl, —NR$^{14}$R$^{15}$, —NR$^{14}$COR$^{15}$, —NHSO$_2$R, —COR$^{14}$, —CO$_2$R$^{14}$, —OR$^{14}$, —OC$_2$H$_4$OR$^{14}$, —SR$^{14}$, —S(O)$_n$R$^{14}$, —S(O)$_n$NR$^{14}$R$^{15}$, —CH(OH)R$^{14}$, —CH$_2$COR$^{14}$, —OC(O)R$^{14}$, —OCHR$^{14}$CO$_2$R$^{15}$, —OCHR$^{14}$COR$^{15}$, —NR$^{14}$CONR$^{14}$R$^{15}$, —NR$^{14}$CO$_2$R$^{15}$, —CONR$^{14}$R$^{15}$, or —CH(OH)C(R$^{14}$)$_3$;

each R$^{18}$ and R$^{19}$ is, independently, at each occurrence, H, $C_1$-$C_6$ alkyl, $C_1$-$C_6$ haloalkyl, or $C_3$-$C_6$ cycloalkyl, wherein each R$^{18}$ and R$^{19}$ is optionally substituted with one or more halogen, hydroxyl, or —CN;

R$^{20}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{21}$, CH$_2$NR$^{21}$R$^{22}$, —CH$_2$OH, —NO$_2$, $C_3$-$C_6$ cycloalkyl, —NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^{21}$ and R$^{22}$ is, independently, at each occurrence, H, —NH$_2$, $C_1$-$C_6$ alkyl, $C_1$-$C_6$ haloalkyl, $C_3$-$C_6$ cycloalkyl, aryl, heteroaryl, or heterocyclyl, wherein each R$^{21}$ and R$^{22}$ is optionally substituted with one or more halogen, hydroxyl, or —CN;

R$^{23}$ is, at each occurrence, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{24}$, CH$_2$NR$^{24}$R$^{25}$, —CH$_2$OH, —NO$_2$, $C_3$-$C_6$ cycloalkyl, —NR$^{24}$R$^{25}$, —NR$^{24}$COR$^{25}$, —NHSO$_2$R, —COR$^{24}$, —CO$_2$R$^{24}$, —OR$^{24}$, —OC$_2$H$_4$OR$^{24}$, —SR$^{24}$, —S(O)$_n$R$^{24}$, —S(O)$_n$NR$^{24}$R$^{25}$, —CH(OH)R$^{24}$, —CH$_2$COR$^{24}$, —OC(O)R$^{24}$, OCHR$^{24}$CO$_2$R$^{25}$, —OCHR$^{24}$COR$^{25}$, —NR$^{24}$CONR$^{24}$R$^{25}$, —NR$^{24}$CO$_2$R$^{25}$, —CONR$^{24}$R$^{25}$, or —CH(OH)C(R$^{24}$)$_3$;

each R$^{24}$ and R$^{25}$ is, independently, at each occurrence, H, —NH$_2$, $C_1$-$C_6$ alkyl, $C_1$-$C_6$ haloalkyl, $C_3$-$C_6$ cycloalkyl, aryl, heteroaryl or heterocyclyl, wherein each R$^{24}$ and R$^{25}$ is optionally substituted with one or more halogen, hydroxyl, or —CN;

Ar$^1$ is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, indazolyl 3,4-dihydro-2H-benzo[1,4]oxazine, benzo[1,3]dioxole, or heterocyclyl, wherein Ar$^1$ is optionally substituted with 1 to 5 R$^{16}$ groups; and wherein two of said R$^{16}$ groups, each attached to adjacent carbon atoms of said Ar$^1$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 R$^{20}$ groups;

$Ar^2$ is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, indazolyl, 3,4-dihydro-2H-benzo[1,4]oxazine, benzo[1,3]dioxole, or heterocyclyl, wherein each $Ar^2$ is optionally substituted with 1 to 5 $R^{17}$ groups; and wherein two of said $R^{17}$ groups, each attached to adjacent carbon atoms of said $Ar^2$, are optionally taken together along with the carbon atoms to which they are attached to form a fused saturated, fused partially unsaturated, or fused unsaturated 5 or 6 membered carbocyclic or heterocyclic ring, wherein said carbocyclic or heterocyclic ring is optionally substituted with 1 to 3 $R^{23}$ groups;

n is 0, 1, or 2;

aryl is phenyl or naphthyl, wherein said aryl is optionally substituted with 1 to 10 substituents independently selected from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, or indazolyl, wherein said heteroaryl is optionally substituted with 1 to 10 substituents selected from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$ or —S(O)$_n$R$^{18}$, —CH(OH)R$^{18}$, —CH$_2$COR$^{18}$, —OC(O)R$^{18}$, —NR$^{18}$CONR$^{18}$R$^9$, —NR$^{18}$CO$_2$R$^{19}$, —CONR$^{18}$R$^{19}$, or —CH(OH)C(R$^{18}$)$_3$; and heterocyclyl is saturated or partially saturated heteroaryl, optionally substituted with 1 to 10 substituents selected from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{18}$R$^{19}$, —NR$^{18}$COR$^{19}$, —COR$^{18}$, —CO$_2$R$^{18}$, —OR$^{18}$, —SR$^{18}$, —S(O)$_n$R$^{18}$, —CH(OH)R$^{18}$, —CH$_2$COR$^{18}$, —OC(O)R$^{18}$, —NR$^{18}$CONR$^{18}$R$^{19}$, —NR$^{18}$CO$_2$R$^{19}$, —CONR$^{18}$R$^{19}$, or —CH(OH)C(R$^{18}$)$_3$.

* * * * *